(12) United States Patent
Liu et al.

(10) Patent No.: US 9,074,938 B2
(45) Date of Patent: Jul. 7, 2015

(54) SUBSTRATE FOR SURFACE ENHANCED RAMAN SPECTROSCOPY ANALYSIS AND MANUFACTURING METHOD OF THE SAME, BIOSENSOR USING THE SAME, AND MICROFLUIDIC DEVICE USING THE SAME

(71) Applicants: Xiaoyan Liu, Seattle, WA (US); Kenji Kitamura, Ibaraki (JP); Minoru Osada, Ibaraki (JP); Takahiro Nagata, Ibaraki (JP); Guozhong Cao, Seattle, WA (US)

(72) Inventors: Xiaoyan Liu, Seattle, WA (US); Kenji Kitamura, Ibaraki (JP); Minoru Osada, Ibaraki (JP); Takahiro Nagata, Ibaraki (JP); Guozhong Cao, Seattle, WA (US)

(73) Assignees: University of Washington, Seattle, WA (US); National Institute for Materials Science, Tsukuba-shi (JP)

( * ) Notice: Subject to any disclaimer, the term of this patent is extended or adjusted under 35 U.S.C. 154(b) by 0 days.

(21) Appl. No.: 13/929,381

(22) Filed: Jun. 27, 2013

(65) Prior Publication Data

US 2014/0002816 A1 Jan. 2, 2014

Related U.S. Application Data

(60) Provisional application No. 61/666,302, filed on Jun. 29, 2012.

(51) Int. Cl.
*G01N 21/75* (2006.01)
*G01J 3/44* (2006.01)
(Continued)

(52) U.S. Cl.
CPC ............... *G01J 3/44* (2013.01); *G01J 3/0291* (2013.01); *B01L 2300/0816* (2013.01);
(Continued)

(58) Field of Classification Search
CPC ............... G01N 21/658; G01N 21/65; G01N 2021/656; G01N 2021/7763; G01N 21/63; G01N 21/6452; G01N 21/6454; G01J 3/44; G01J 3/28; G01J 3/0272; G01J 3/0291; G01J 3/10; G01J 3/46; G01J 3/51; G02B 6/0229; G02B 5/008; C09K 19/0225; B01L 2200/12; B01L 3/5027; B01L 2200/10; B01L 2300/0636; B01L 2300/0816; B01L 2300/0819
USPC ............... 422/52, 82.05, 82.06, 82.07, 82.08, 422/82.09, 82.11, 407, 500, 501, 502, 503, 422/504, 930; 435/164, 165, 283.1, 287.1, 435/287.2, 288.7, 808, 4, 5, 7.2, 7.9; 436/52, 53, 164, 165, 172, 174, 518, 436/524, 525, 526, 805, 809
See application file for complete search history.

(56) References Cited

U.S. PATENT DOCUMENTS 5,527,712 A 6/1996 Sheehy
6,781,690 B2 8/2004 Armstrong
(Continued)

FOREIGN PATENT DOCUMENTS

JP 2005-077362 A 3/2005
JP 2007-198933 A 8/2007
WO 2006/113783 A1 10/2006

OTHER PUBLICATIONS

Liu, X., et al., "Photocatalytic Nanoparticle Deposition on LiNbO$_3$ Nanodomain Patterns Via Photovoltaic Effect," Applied Physics Letters 91(4):044101-1-044101-3, Jul. 2007.

*Primary Examiner* — Dennis M White
(74) *Attorney, Agent, or Firm* — Christensen O'Connor Johnson Kindness PLLC

(57) ABSTRACT

A substrate for surface enhanced Raman spectroscopy analysis (SERS) comprises a ferroelectric single crystal having polarization-inverted patterns of spontaneous polarizations including polarization-inverted portions and non-inverted polarization portions, and metallic dots positioned at only either one polarized surfaces of the polarization-inverted portions and the non-inverted polarization portions. The provided SERS substrate produces a high enhancement effect. A microfluidic device incorporating the SERS substrate is also provided.

11 Claims, 26 Drawing Sheets

(51) Int. Cl.
*G01J 3/02* (2006.01)
*G01N 21/64* (2006.01)
*B01L 3/00* (2006.01)
*G01N 21/65* (2006.01)
*G01N 21/63* (2006.01)
*G01N 21/77* (2006.01)

(52) U.S. Cl.
CPC ........ *G01N 21/6454* (2013.01); *B01L 2200/12* (2013.01); *G01N 21/6452* (2013.01); *B01L 2200/10* (2013.01); *B01L 3/5027* (2013.01); *G01N 2021/656* (2013.01); *G01N 21/65* (2013.01); *G01N 21/63* (2013.01); *G01N 2021/7763* (2013.01); *B01L 2300/0636* (2013.01); *B01L 2300/0819* (2013.01); *G01N 21/658* (2013.01)

(56) References Cited

U.S. PATENT DOCUMENTS

| | | |
|---|---|---|
| 7,323,227 B2 | 1/2008 | Fudoji |
| 7,586,166 B2 | 9/2009 | Bonnell |
| 8,193,499 B2 | 6/2012 | Nagao |
| 2006/0034729 A1* | 2/2006 | Poponin ................. 422/82.05 |

\* cited by examiner

SUBSTRATE FOR SURFACE ENHANCED RAMAN SPECTROSCOPY ANALYSIS AND MANUFACTURING METHOD OF THE SAME, BIOSENSOR USING THE SAME, AND MICROFLUIDIC DEVICE USING THE SAME

CROSS-REFERENCE TO RELATED APPLICATION

This application claims the benefit of U.S. Provisional Patent Application No. 61/666,302, filed Jun. 29, 2012, the disclosure of which is incorporated herein by reference in its entirety.

TECHNICAL FIELD

The present invention relates to a substrate for surface enhanced Raman spectroscopy analysis (SERS) and a manufacturing method of the same, a biosensor using the same, and a microfluidic device using the same.

BACKGROUND

It has been known a phenomenon in which when a material is irradiated with a light, a different wavelength output light is observed by modulating the original light due to the vibration or rotation of molecules or crystal. This phenomenon is called as Raman effect. The Raman effect is utilized as a method (Raman spectroscopy) to investigate a structure of a state of a molecule and so on as well as an infrared spectroscopy.

However, since the intensity of the Raman scattering light is very weak in comparison with the Rayleigh scattering light which occupies a majority of the scattering light, it has a defect that it is difficult to analyze a molecular structure having a very thin film such as a monomolecular layer formed on a surface on a substrate by the Raman spectroscopy.

For this reason, it has been proposed a surface enhanced Raman spectroscopy analysis (hereinafter, also referred to as SERS) utilizing a surface enhanced Raman spectroscopy. The surface enhanced Raman scattering is a phenomenon in which an intensity of Raman scattering light absorbed on or in a metal such as silver or gold, and the enhancement of an order of 103 to 106, usually. Therefore, the analysis can be performed at high sensitivity and is utilized for the analysis of a mechanism of a chemical reaction on a surface of an electrode (Japanese Patent Publication No. 2005-77362 and Japanese Patent Publication No. 2007-198933).

On the other hand, substrates for surface enhanced Raman spectroscopy analysis have been manufactured and marketed, in which a gold is coated on a nanoprocessed surface of silicone, metal nanoparticles are adhered and fixed on a slide glass, Au nanorod arrays are formed on a slide glass, and so on.

However, the first type such conventional SERS substrates have an enhancement factor of an order of $10^6$ or so at most, their manufacturing method is complicated, and it is unable to reuse by cleaning the surface thereof.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The present invention has been accomplished in consideration of the above-mentioned circumstance and for clearing up the above prior art problems one for all, and an object of the present invention is to provide a substrate for surface enhanced Raman spectroscopy analysis (SERS substrate) which has an extremely large of the enhancement factor compared with the conventional ones, which can be used repeatedly by cleaning it, and which can be applied to a microfluidic device.

It is another object of the present invention to provide a method for manufacturing the above SERS substrate in a very convenient manner.

It is still another object of the present invention to provide a biosensor which can detect biomaterial, biomolecule or the like with excellent reproducibility and with very high precision.

It is still another object of the present invention to provide a microfluidic device which can perform an analysis for biomolecule or the like with excellent reproducibility and with very high precision.

The inventors of this application have found that silver nanoparticles have deposited on a surface of the polarization-inverted nanodomains of lithium niobate ($LiNbO_3$) which is a ferroelectric crystal by dropping $AgNO_3$ aqueous solution on the surface and irradiating the dropped portion with UV light, and have reported it in Appl. Phys. Lett. 91, pp. 044101-1 to -3, 2007, which is incorporated herein by reference in its entirety.

The inventors of the present application have investigated earnestly to realize a SERS substrate having a very large enhancement factor which has been proposed heretofore, by using various ferroelectric single crystals based on the above findings. As a result, the present invention has been accomplished.

According to first aspect of the invention, there is provided a substrate for surface enhanced Raman spectroscopy analysis, comprising a ferroelectric single crystal having polarization-inverted patterns of spontaneous polarizations including polarization-inverted portions and non-inverted polarization portions; and metallic dots positioned on only one of the polarized surfaces selected from the group consisting of the polarization-inverted portions and the non-inverted polarization portions.

In the above invention, the ferroelectric single crystal may be a lithium niobate, a lithium tantalate or a lead zirconate.

In the above invention, the polarization-inverted patterns may satisfy a condition that an area ratio of the positive polarity surfaces to the negative polarity surfaces is in a range of from 0.25 to 4.

In the above invention, the metallic dots may have diameter of from 10 nm to 200 nm.

In the above invention, the metallic dots may have diameter of from 50 nm to 150 nm.

In the above invention, the metallic dots may be positioned at an interval of from 50 nm to 150 nm.

In the above invention, the metallic dots may comprise one member selected from the group consisting of Au, Ag, Pt, Pd, Rh, Ni, Co, Fe and an alloy thereof.

According to second aspect of the invention, there is provided a manufacturing method of a substrate for surface enhanced Raman spectroscopy analysis, comprising: a step of providing a solution including metal to a ferroelectric single crystal having polarization-inverted patterns of spontaneous polarizations including polarization-inverted portions and non-inverted polarization portions; and a step of irradiating the ferroelectric single crystal provided with the solution with a light.

In the above invention, a concentration of the solution may be in the range of from $10^{-4}$ M to $10^{-3}$ M.

In the above invention, the light may be ultraviolet light, a visible light or white light.

In the above invention, the irradiation time in the step of irradiating the ferroelectric single crystal with the light may be from 30 seconds to 25 minutes.

According to third aspect of the invention, there is provided a microfluidic device for surface enhanced Raman spectroscopy analysis, including: a base plate; and a microfluidic path formed on the base plate in which fluid flows; and wherein the above substrate for surface enhanced Raman spectroscopy analysis is provided on the base plate.

According to fourth aspect of the invention, there is provided a microfluidic device for surface enhanced Raman spectroscopy analysis, including: a base plate; and a microfluidic path formed on the substrate in which fluid flows; and wherein the base plate comprises a ferroelectric single crystal; at least one of the portion of the ferroelectric single crystal has polarization-inverted patterns of spontaneous polarizations including polarization-inverted portions and non-inverted polarization portions; and metallic dots are positioned on only one of the polarized surfaces selected from the group consisting of the polarization-inverted portions and the non-inverted polarization portions.

According to fifth aspect of the invention, there is provided a biosensor using the above substrate for surface enhanced Raman spectroscopy analysis.

The substrate for surface enhanced Raman spectroscopy analysis comprises a ferroelectric single crystal having polarization-inverted patterns of spontaneous polarizations including polarization-inverted portions and non-inverted polarization portions, and metallic dots positioned at only either one polarized surfaces of the polarization-inverted portions and non-inverted polarization portions. Since the metallic dots are arranged uniformly in self-organized manner, they exhibit high SERS activity (enhancement factor of $10^8$ or more). Further, in the case where a lithium niobate or a lithium tantalate having acid-resistance and alkali-resistance is adopted as a ferroelectric single crystal, the SERS substrate can be used repeatedly by washing it with acid or alkali, which is environmentally friendly. Such SERS substrate applied to a microfluidic device can serve as a biosensor.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1A:
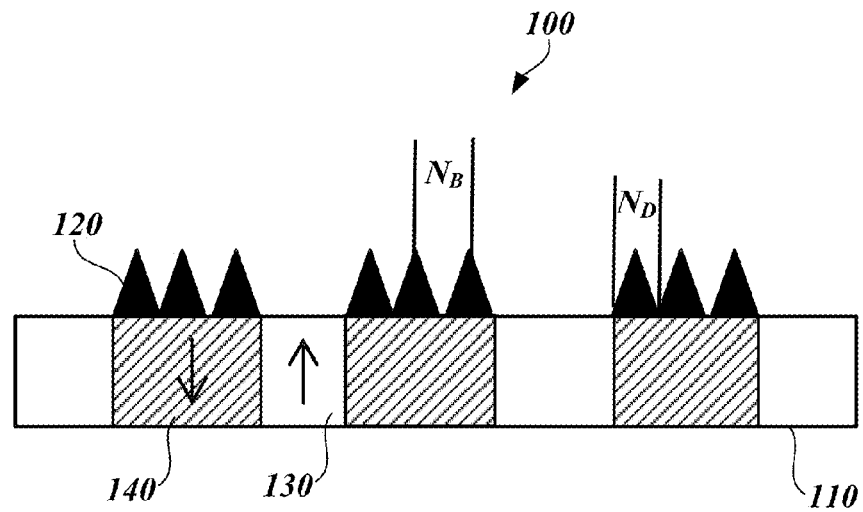
FIGS. 1A and 1B are schematic views of a substrate for surface enhanced Raman spectroscopy of the invention.

While illustrative embodiments have been illustrated and described, it will be appreciated that various changes can be made therein without departing from the spirit and scope of the invention.

The invention will be described in detail by way of the preferred embodiments with reference to the accompanying drawings. In the drawings, a similar reference numeral is assigned to a similar element or part and its explanation is omitted.

Embodiment 1

A substrate for surface enhanced Raman spectroscopy analysis (SERS) and a manufacturing method of the same of the invention will be described hereinafter.

Figure 1B:
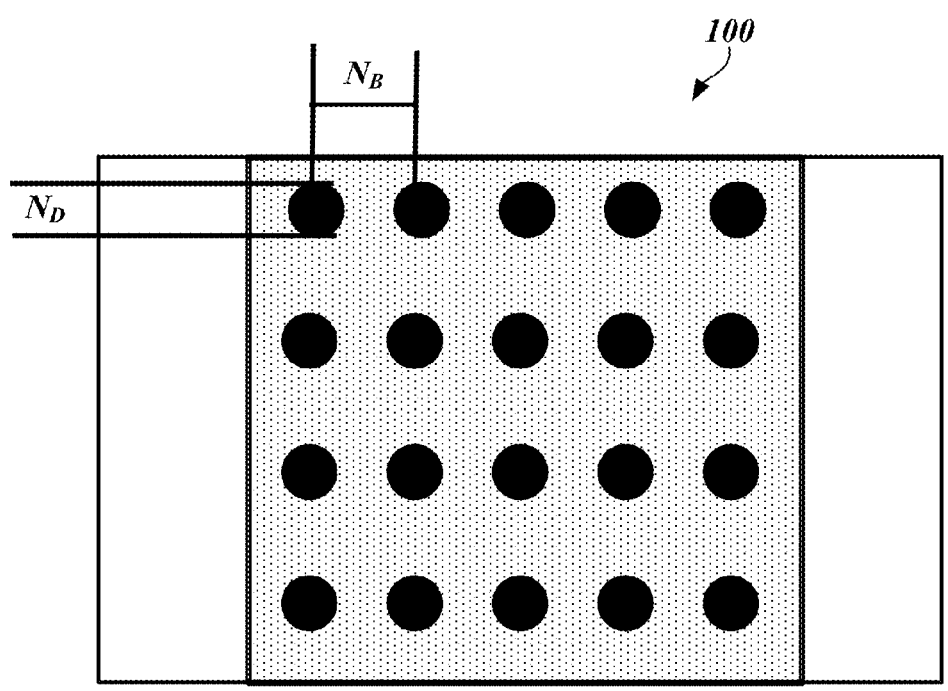

FIGS. 1A and 1B are schematic views of a substrate for surface enhanced Raman spectroscopic analysis (SERS) of the invention.

FIG. 1A is a cross-sectional view of the SERS substrate of the invention, and FIG. 1B is a plan view of the SERS substrate of the invention. The SERS substrate of the invention comprises a ferroelectric single crystal 110 and metallic dots 120 positioned thereon.

Specifically, the ferroelectric single crystal 110 has polarization-inverted patterns of spontaneous polarizations including non-inverted polarization portions 130 and polarization-inverted portions 140. In FIG. 1A, the polarization-inverted portions are periodic. In the drawing, the regions indicated with white color are the non-inverted polarization portions and the regions indicated with black color are the polarization-inverted portions. The surfaces of the non-inverted polarization portions 130 have an opposite polarity of those of the polarization-inverted portions 140. For example, the surfaces of the non-inverted polarization portions 130 may have a negative polarity, and the surfaces of the polarization-inverted portions 140 may have a positive polarity. The arrows in the drawing indicate the directions of the spontaneous polarizations of the ferroelectric single crystal 110, and it is understood that the non-inverted polarization portions 130 and the polarization-inverted portions 140 have the opposite polarization directions with respect to one another.

The ferroelectric single crystal 110 is not limited specifically a single crystal comprising an arbitrary ferroelectric material having uniaxial polarizations, but preferred are a congruent lithium niobate (CLN), a congruent lithium tantalate (CLT), a stoichiometric lithium niobate (SLN), a stoichiometric lithium tantalate (SLT), additive doped material of these compound (doped-CLN, doped-CLT, doped-SLN, doped-SLT), and lead zirconate titanate (PZT), in view of easy-to-form polarization-inverted patterns and controllability. The additive may include Mn, Mg, Zn, Sr or the like, and adds in order to improve controllability of the composition and resistance to optical damage. In the specification, CLN and SLN are collectively-referred as simply lithium niobate (LN), and CLT and SLT are collectively-referred as simply lithium tantalate (LT), if specific mention is not done. The more preferable ferroelectric single crystal 110 may be LN and LT having acid-resistance and alkali-resistance. By adopting LN and LT, when the metallic dots 120 have acid resistance or alkali-resistance, the SERS substrate can be used repeatedly by washing it with acid or alkali.

Figure 2A:
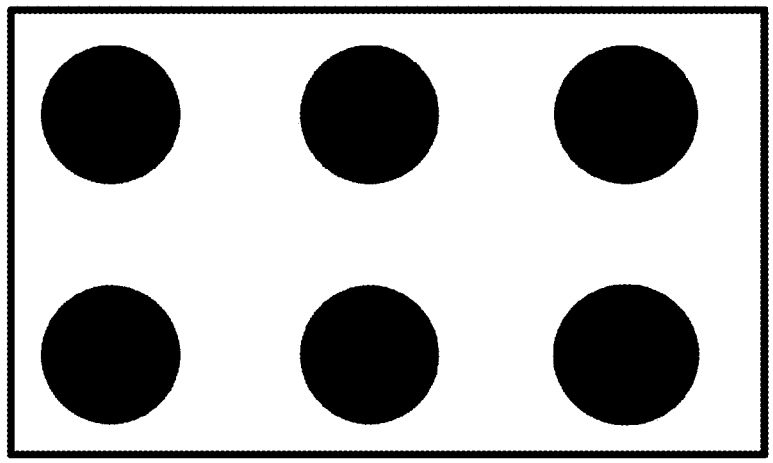
FIGS. 2A and 2B are schematic views of exemplary polarization-inverted patterns.
Figure 2B:
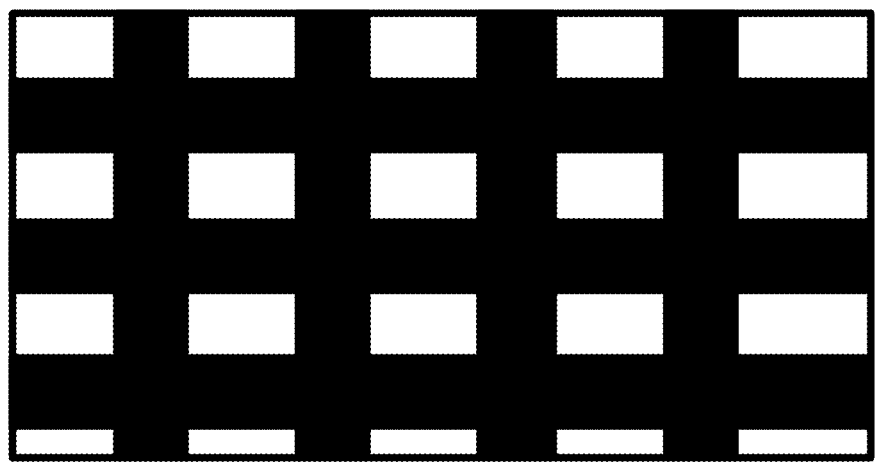

FIGS. 2A and 2B are schematic views showing exemplified polarization-inverted patterns.

As shown in FIGS. 1A and 1B, the polarization-inverted patterns include the non-inverted polarization portions 130 and the polarization-inverted portions 140. Similar to FIGS. 1A and 1B, in FIGS. 2A and 2B, the regions indicated with white color are the non-inverted polarization portions and the regions indicated with black color are the polarization-inverted portions. The polarization-inverted patterns may be periodic as shown in FIGS. 1A and 1B, dot-shaped as shown in FIG. 2A, or lattice-shaped as shown in FIG. 2B. The patterns are not particularly limited; they are multi-polarization-inverted patterns including a plurality of the non-inverted polarization portions 130 and a plurality of the polarization-inverted portions 140.

For example, when the ferroelectric single crystal 110 comprises LN or LT, the surfaces of the non-inverted polarization portions 130 have a negative polarity (also referred to as −Z surfaces), and the surfaces of the inverted-polarization portions 140 had a positive polarity (also referred to as +Z surfaces). An area ratio of the positive polarity surfaces to the negative polarity surfaces (the area of the positive polarity surfaces/the area of the negative polarity surfaces) is preferably in a range of from 0.25 to 4. With this condition, the metallic dots 120 as explained hereinafter in detail can be positioned only on the surfaces of the polarization-inverted portions 140, namely, only on the positive polarity surfaces, uniformly.

Such polarization-inverted patterns may be formed by a method of applied electric field using lithography, a piezo response scanning method using piezoelectric response, or the like.

Turning to FIGS. 1A and 1B, the metallic dots 120 are indicated only on the polarization-inverted portions 140. Alternatively, the metallic dots 120 may be positioned only on the non-inverted polarization portions 130. In other words, the metallic dots 120 may be positioned on only either one polarized surfaces of the non-inverted polarization portions 130 and the polarization-inverted portions 140, included in the polarization-inverted patterns. Whether the metallic dots 120 are positioned on either polarized surfaces depends on the kind of the metallic dots 120 and/or the kind of the ferroelectric single crystal 110.

The material of the metallic dots 120 may comprise one member selected from the group consisting of Au, Ag, Pt, Pd, Rh, Ni, Co, Fe and an alloy thereof. These materials exhibit an excellent SERS activity.

For example, when the metallic dots 120 comprise gold or silver and the ferroelectric single crystal 110 comprises LN or LT, the metallic dots 120 are positioned only on the surfaces of the polarization-inverted portions 140. On the other hand, for example, when the metallic dots 120 comprise nickel and the ferroelectric single crystal 110 comprises PZT, the metallic dots 120 are positioned only on the non-inverted polarization portions 130. When the ferroelectric single crystal 110 comprises LN, LT or PZT, the surfaces of the non-inverted polarization portions 130 are −Z surfaces and the surfaces of the polarization-inverted portions 140 are +Z surfaces. In this manner, the metallic dots 120 are positioned on only either one polarized surfaces of non-inverted polarization portions 130 and the polarization-inverted portions 140, included in the polarization-inverted patterns.

As shown in FIGS. 1A and 1B, each of the metallic dots 120 has a conical taper shape. The metallic dots 120 have diameter (average diameter) $N_D$ of from 10 nm to 200 nm. When the diameter $N_D$ of the metallic dots is within the above range, the SERS substrate of the invention can be manufactured with good controllability and exhibits an excellent SERS activity. Preferably, the metallic dots 120 have diameter $N_D$ of from 50 nm to 150 nm. When the diameter $N_D$ of the metallic dots is within the above range, the SERS substrate of the invention can be manufactured with good controllability and exhibits a more excellent SERS activity. As shown in FIGS. 1A and 1B, the metallic dots 120 are positioned at an interval (average interval) $N_B$ of from 10 nm to 200 nm, and from 50 nm to 150 nm, preferably. It is preferable that the interval $N_B$ of the metallic dots 120 coincides with the diameter $N_D$ thereof. In this manner, the metallic dots 120 are arranged to be distributed uniformly, exhibiting the excellent SERS activity.

Although the metallic dots 120 are shown to be separated and scattered in FIGS. 1A and 1B for simplicity, it should be noted that, in face, the metallic dots 120 are closely positioned. Further, although the metallic dots 120 of single layer are positioned on the ferroelectric single crystal 110, the metallic dots 120 may be multi-layer. Also, in this case, the dot diameter $N_D$ and the dot interval $N_B$ of the metallic dots 120 are preferably within the above range.

Next, it will be explained the process of manufacturing the SERS substrate of the invention.

Figure 3:
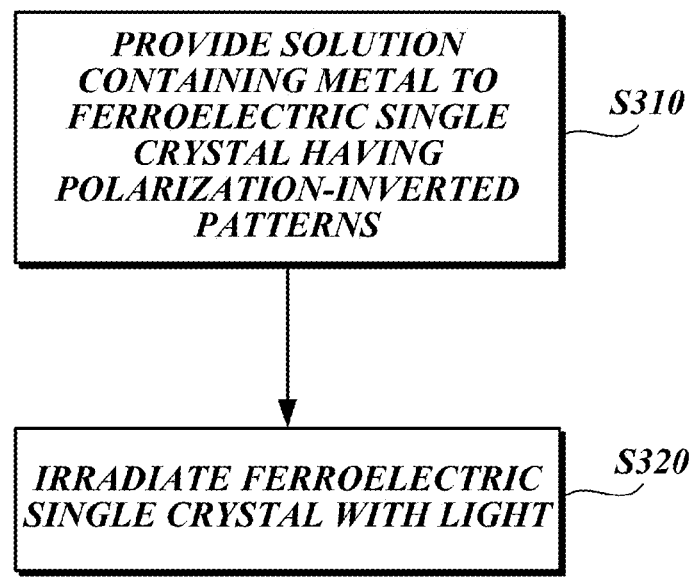
FIG. 3 is a flowchart of process of manufacturing the SERS substrate of the invention.
Figure 4:
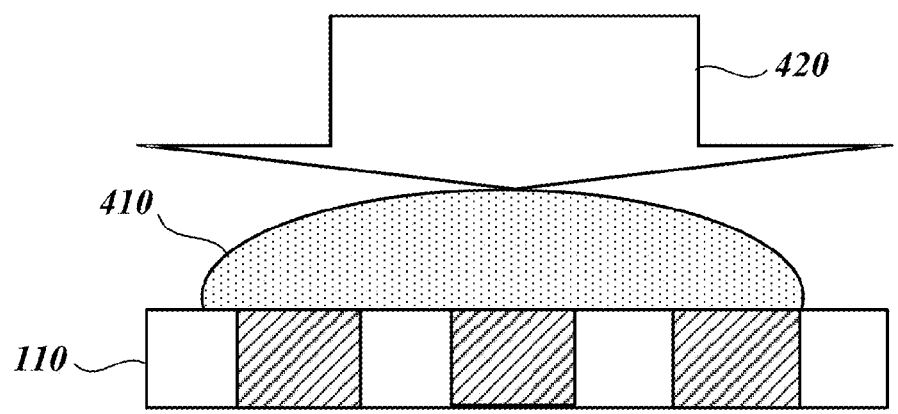
FIG. 4 is a schematic view of procedure of manufacturing the SERS substrate of the invention.

FIG. 3 is a flowchart of process of manufacturing the SERS substrate of the invention and FIG. 4 is a schematic view of a process of manufacturing the SERS substrate of the invention (e.g., by the steps illustrated in FIG. 3).

Referring to FIGS. 3 and 4, in step S310, a solution 410 containing a metal is provided to the ferroelectric single crystal 110 having the polarization-inverted patterns of the spontaneous polarizations including the polarization-inverted portions and the non-inverted polarization portions. Herein, since the ferroelectric single crystal 110 is the same as shown in FIGS. 1A and 1B, the explanation thereof is omitted.

The solution 410 including the metal is a salt solution containing the metal selected from the group consisting of Au, Ag, Pt, Pd, Rh, Ni, Co, Fe and an alloy thereof. When the metal comprises silver, the solution 410 may be $AgNO_3$ aqueous solution, for example. The skilled person can select such solution arbitrarily. The provision of the solution 410 containing the metal may be conducted by dropping it on the ferroelectric single crystal 110, coating it thereon, or immersing it thereinto.

A concentration of the solution 410 containing the metal is preferably in the range of from $10^{-4}$ M to $10^{-3}$ M. When the concentration of the solution 410 is within this range, it is easy to form the metallic dots 120 having the above dot diameter $N_D$ and dot interval $N_B$.

In step S320, the ferroelectric single crystal 110 provided with the solution 410 containing the metal is irradiated with a light 420. The light 420 may be ultraviolet light, a visible light or white light. As the light 420, there may be selected any type of light with a wavelength enabling excitation of impurities in the ferroelectric single crystal 110, or exceeding the band gap of the ferroelectric single crystal 110 and transmitting through the ferroelectric single crystal 110. In other words, the light having the wavelength enabling to excite impurities in the ferroelectric single crystal 110, or exceeding the band gap of the ferroelectric single crystal 110, the electrons in the ferroelectric single crystal 110 are excited, so that the metal ions in the solution 410 containing the metal are deposited and fixed. Further, by selecting the light having the wavelength transmitting through the ferroelectric single crystal 110, not only the electrons near the surface of the ferroelectric single crystal 110 but also those of overall the thickness direction can be sufficiently excited.

A light source of the light 420 may be a laser source emitting a laser having single wavelength, mercury lamp, xenon lamp, or mercury xenon lamp emitting white light. When the metal ions in the solution 410 are irradiated with the light 420, the metal ions are fixed in a self-organized manner only on either one polarized surfaces of the polarization-inverted patterns of the ferroelectric single crystal 110, to be disposed as the metallic dots 120.

When thus fixed metallic dots 120 comprise gold, and the ferroelectric single crystal 110 comprises LN or LT, the properties of the metallic dots 120 cannot be changed by using the SERS substrate of the invention repeatedly by washing it with acid or alkali, exhibiting the stable characteristics.

In step S320, the dot diameter $N_D$ and the dot interval $N_B$ of the metallic dots 120 can be made larger by setting the irradiation time of the light 420 longer. This enables control of the degree of the SERS activity of the SERS substrate of the invention. The irradiation time of the light is preferably from 30 seconds to 25 minutes. Similarly, the dot diameter $N_D$ and the dot interval $N_B$ of the metallic dots 120 can be controlled by adjusting the intensity of the irradiating light 420 and/or the concentration of the solution 410.

Embodiment 2

A microfluidic device using the SERS substrate of the invention explained in the Embodiment 1 will be described.

Figure 5A:
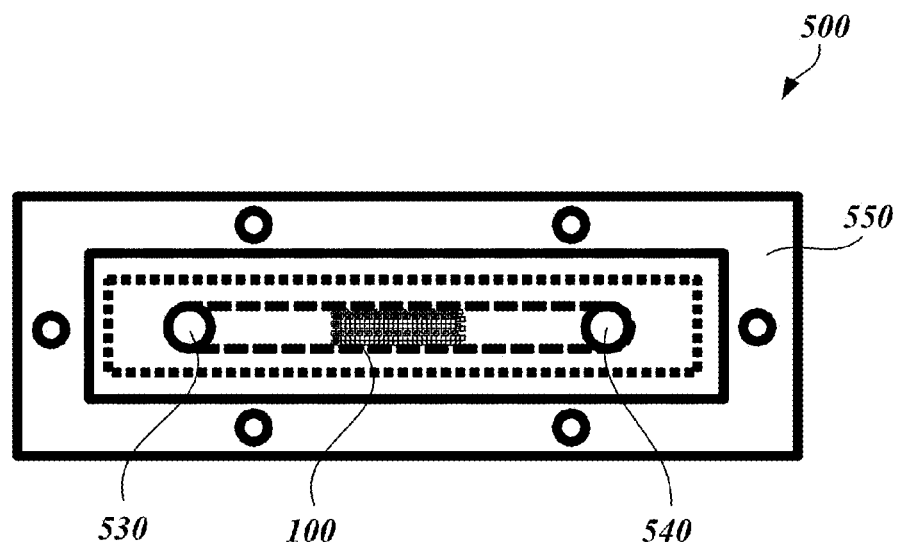
FIGS. 5A and 5B are schematic views of a microfluidic device of the invention.
Figure 5B:
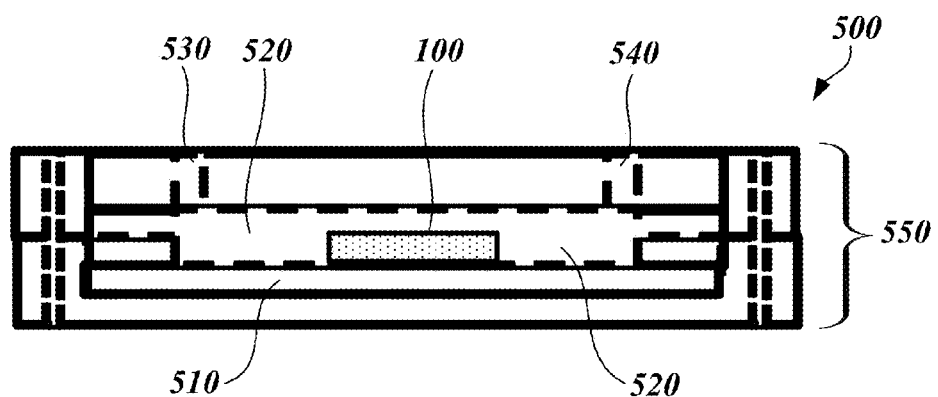

FIGS. 5A and 5B are schematic views of the microfluidic device of the invention.

The microfluidic device 500 is provided with a base plate 510 and a microfluidic path 520 formed on the base plate 510 in which fluid flows, and the SERS substrate 100 is provided on the base plate 510. Since the SERS substrate 100 is the same as explained in the Embodiment 1, the explanation thereof is omitted. As shown in FIG. 5, the base plate 510, the microfluidic path 520 and the SERS substrate 100 are disposed in a housing 550 provided with an inlet port 530 and a drain port 540. The base plate 510 may comprise a slide glass, for example. The housing 550 may comprise a transparent material that enables transmission of light through the microfluidic path 520 to the SERS substrate. For example, the material may be a silica glass.

Although the base plate 510 and the housing 550 comprise separate members in FIG. 5B, the base plate 510 may be a part of the housing 550.

Figure 6A:
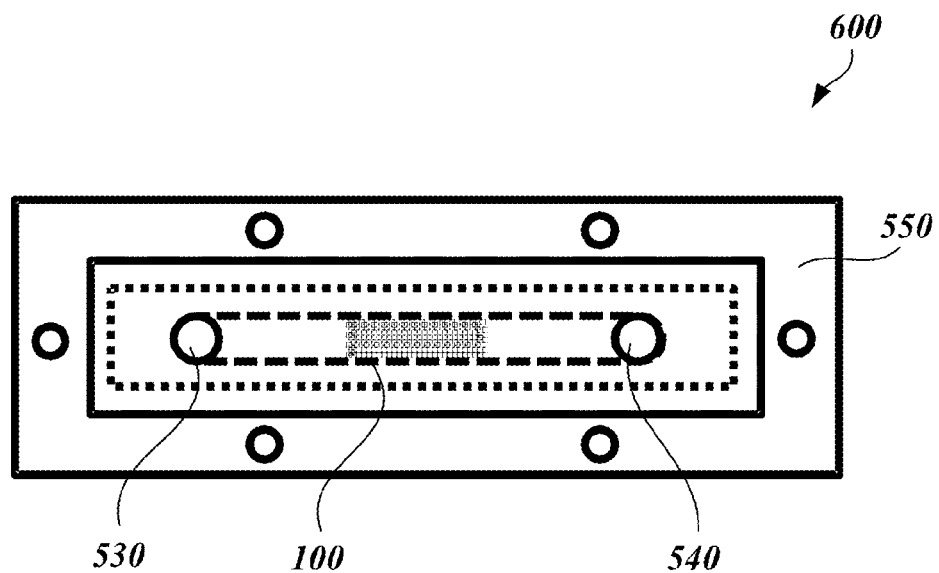
FIGS. 6A and 6B are schematic views of another microfluidic device of the invention.
Figure 6B:
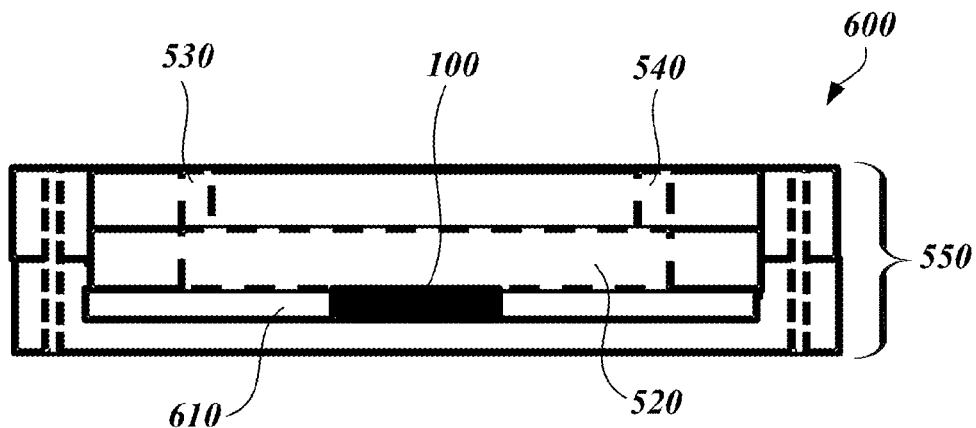

FIGS. 6A and 6B are schematic views of another microfluidic device of the invention.

The microfluidic device 600 of FIGS. 6A and 6B is provided with a base plate 610 and the microfluidic path 520 formed on the base plate 610 in which fluid flows, and the SERS substrate 100 is formed as at least a part of the base plate 610. The microfluidic device 600 of FIGS. 6A and 6B is different from the microfluidic device 500 of FIGS. 5A and 5B in that the base plate 610 comprises the ferroelectric single crystal as explained in the Embodiment 1, and the at least a part of the base plate 610 is formed as the SERS substrate 100. Since at least a part of the base plate 610 comprises the SERS substrate 100, some parts or elements of the base plate 510 in FIGS. 5A and 5B become unnecessary and it is advantageous in cost reducing.

Figure 7:
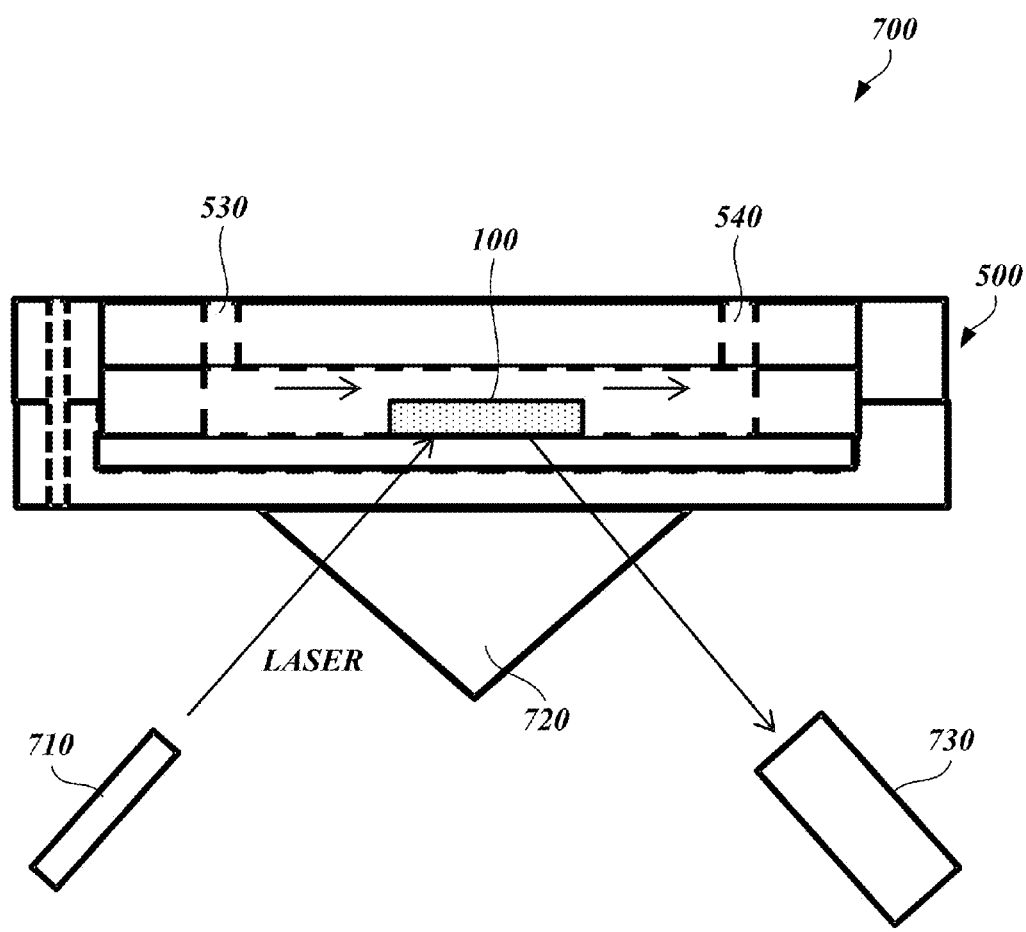
FIG. 7 is a view showing an analysis system of a surface plasmon resonance spectroscopy analysis using the microfluidic device of the invention.

FIG. 7 is a view showing an analysis system of a surface plasmon resonance spectroscopy system using a microfluidic device of this invention.

The analysis system 700 of the surface plasmon resonance spectroscopy analysis includes a light source 710, a prism 720 for refracting the light emitted from the light source 710, the microfluidic device 500 of the invention disposed so as to deliver the refracted light by the prism 720 to the SERS substrate 100 of the invention, and a detector 730 for detecting the light reflected by the SERS substrate 100.

The SERS substrate 100 of the microfluidic device 500 of the invention is irradiated with the light from the light source 710. The light from the light source 710 is reflected by the surfaces of the metallic dots 120 of the SERS substrate 100 and detected by the detector 730. In this case, the detection angle θ is detected by the detector 730.

Next, a test fluid including an analyte (e.g., a biomolecule or the like) is injected via the inlet port 530 into the microfluidic device 500 of the invention. The analyte in the injected test fluid is adsorbed to the metallic dots 120 of the SERS substrate 100 during the flow through the microfluidic path 520 of the microfluidic device 500. As a result, the generation state of the surface plasmon changes. Here, the SERS substrate 100 of the microfluidic device 500 is irradiated again with the light from the light source 710. The light from the light source 710 is reflected by the surfaces of the metallic dots 120 of the SERS substrate 100, and is detected by the detector 730. In this case, the detection angle θ' is detected by the detector 730. The adsorption amount of the analyte can be measured quantitatively from the shift Δ (θ-θ') of the detection angle.

Figure 8:
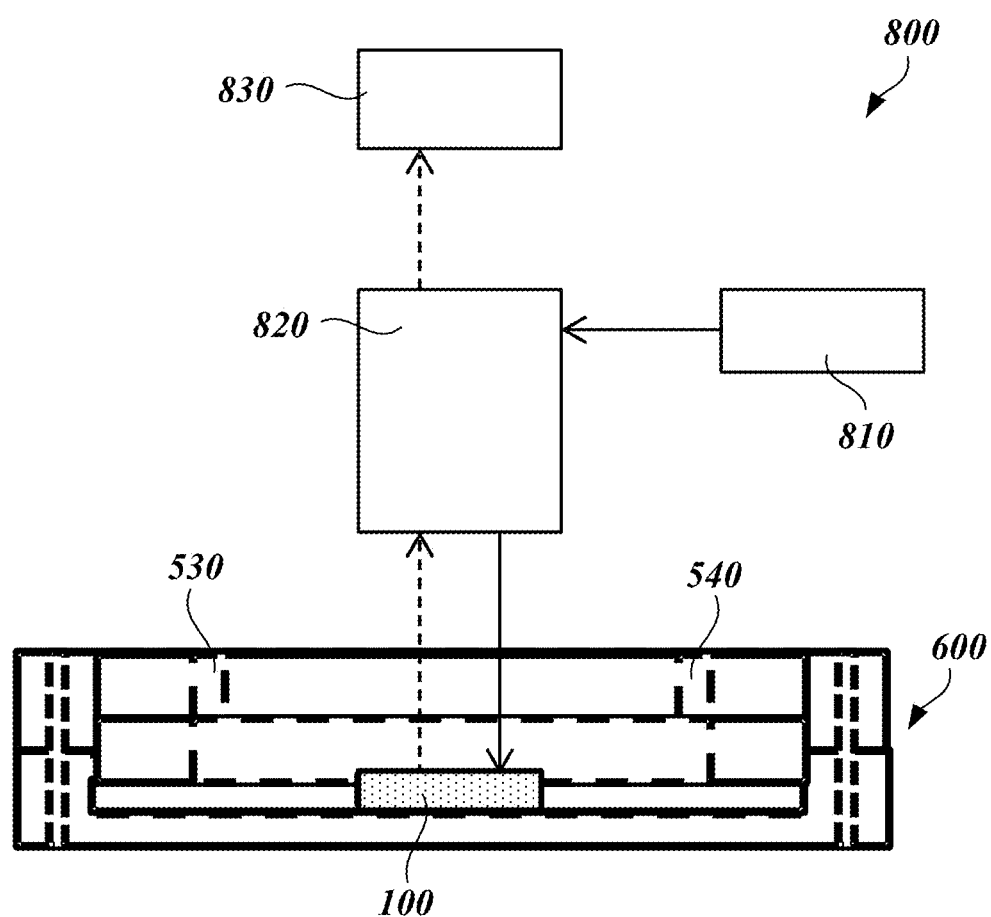
FIG. 8 is a view showing an analysis system of a laser Raman microscopic method and a localized surface plasmon resonance spectroscopy analysis using the microfluidic device of the invention.

FIG. 8 is a view showing an analysis system of a laser Raman microscopic method and a localized surface plasmon resonance spectroscopy analysis using the microfluidic device of the invention.

An analysis system 800 of the laser Raman microscopic method and a localized surface plasmon resonance spectroscopy analysis includes a light source 810, a microscope 820, the microfluidic device 600 of the invention, and a spectrometer 830.

A test fluid including an analyte (e.g., a biomolecule or the like) is injected via the inlet port 530 into the microfluidic device 600 of the invention. The analyte in the injected test fluid is adsorbed to the metallic dots 120 of the SERS substrate 100 during the flow through the microfluidic path 520 of the microfluidic device 600. Here, the SERS substrate 100 of the microfluidic device 600 is irradiated with the light from the light source 810 via the microscope 820. The light from the light source 810 is scattered by the biomolecule adsorbed to the metallic dots 120 of the SERS substrate 100. The scattered light is detected by the spectrometer 830.

The shift amount of the scattered light detected is obtained as a Raman spectrum. The analyte is identified from the Raman spectrum, to measure the adsorbed amount quantitatively. This method can detect a single adsorbed analyte; therefore, ultrasensitive measurement can be realized.

The test fluid is not limited to liquid, and gas may be used.

In FIG. 7, the microfluidic device 500 may be used instead of the microfluidic device 600. In FIG. 8, the microfluidic device 600 may be used instead of the microfluidic device 500.

The following examples are provided for the purposes of illustrating, not limiting, the embodiments provided herein.

Example 1

Example 1 concerns a SERS substrate in which a ferroelectric single crystal comprises CLN, metallic dots comprise silver dots, and polarization-inverted patterns are periodic.

Figure 9A:
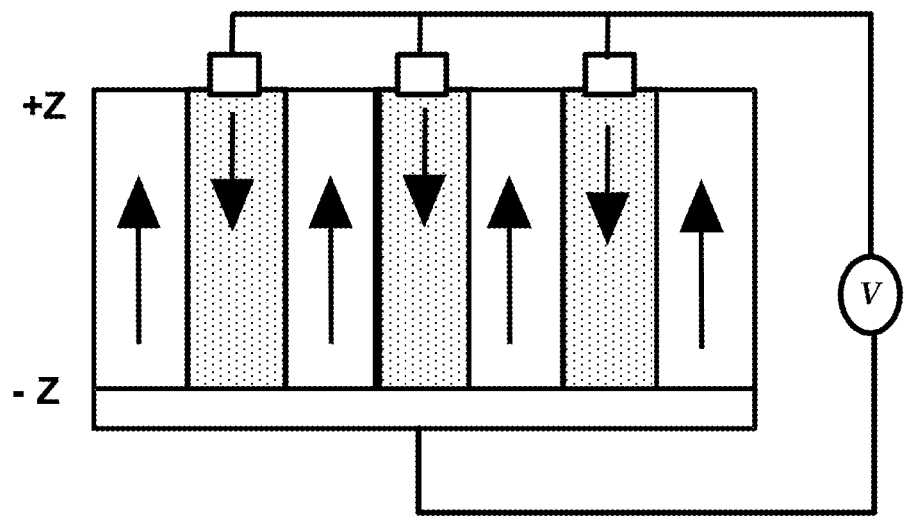
FIGS. 9A and 9B are views showing situations for forming periodic structures in the CLN substrates of Example 1 and Example 5, respectively.
Figure 9B:
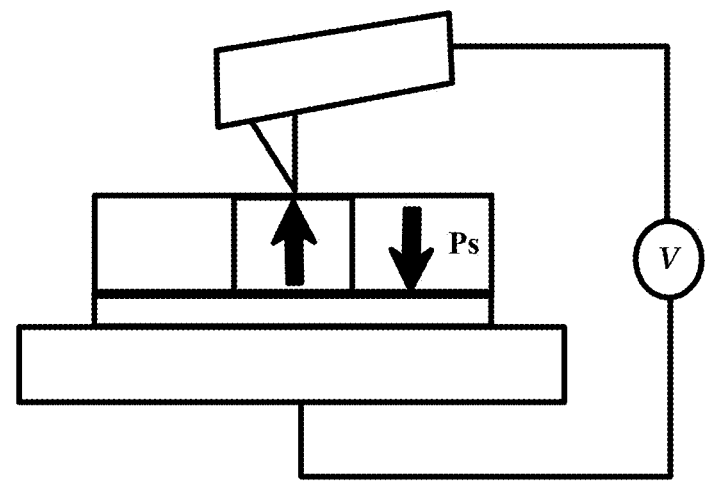

FIGS. 9A and 9B are views showing situations for forming periodic structures in the CLN substrates of Example 1 and Example 5, respectively.

The thickness of the ferroelectric single crystal in the polarization direction was 0.3 mm. Periodic electrodes are formed in the ferroelectric single crystal by using lithography. A width of each period of the periodic electrodes (corresponding to the width of the inverted-polarization) was 15 μm. Periodical polarization-inverted patterns were formed in the CLN substrate by a method of applied electric field as shown in FIG. 9A. The formation of the periodical polarization-inverted patterns was confirmed by atomic force microscopy (AFM). The area ratio of the positive polarity surfaces to the negative polarity surfaces (the area of the positive polarity surfaces/the area of the negative polarity surfaces) was about 1.

Next, 100 μL of $AgNO_3$ aqueous solution ($10^{-3}$ M) was dropped on the CLN substrate having the periodic polarization-inverted patterns (step S310 of FIG. 3), and then the surface of the CLN substrate was irradiated with white light from mercury xenon lamp (30 W) for 3 minutes (step S320 of FIG. 3). Excess $AgNO_3$ aqueous solution was removed and dried.

Figure 10A:
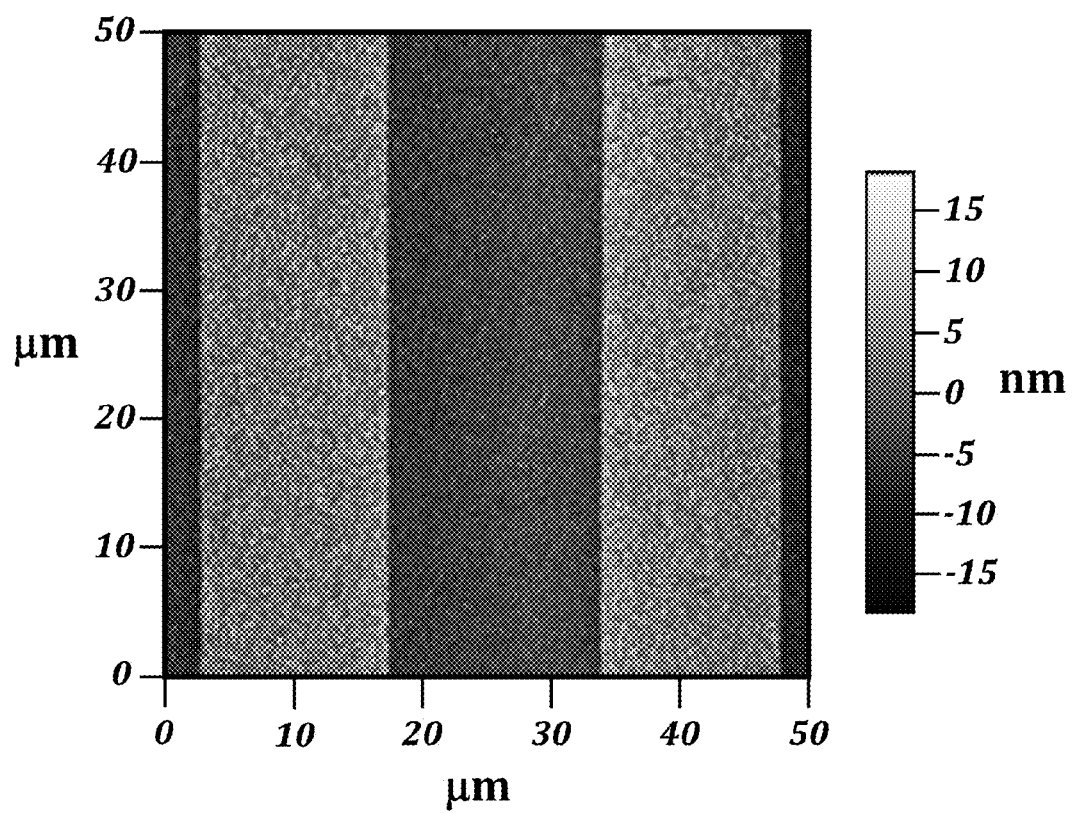
FIGS. 10A-10C are atomic force microscope (AFM) images of the sample of Example 1.
Figure 10B:
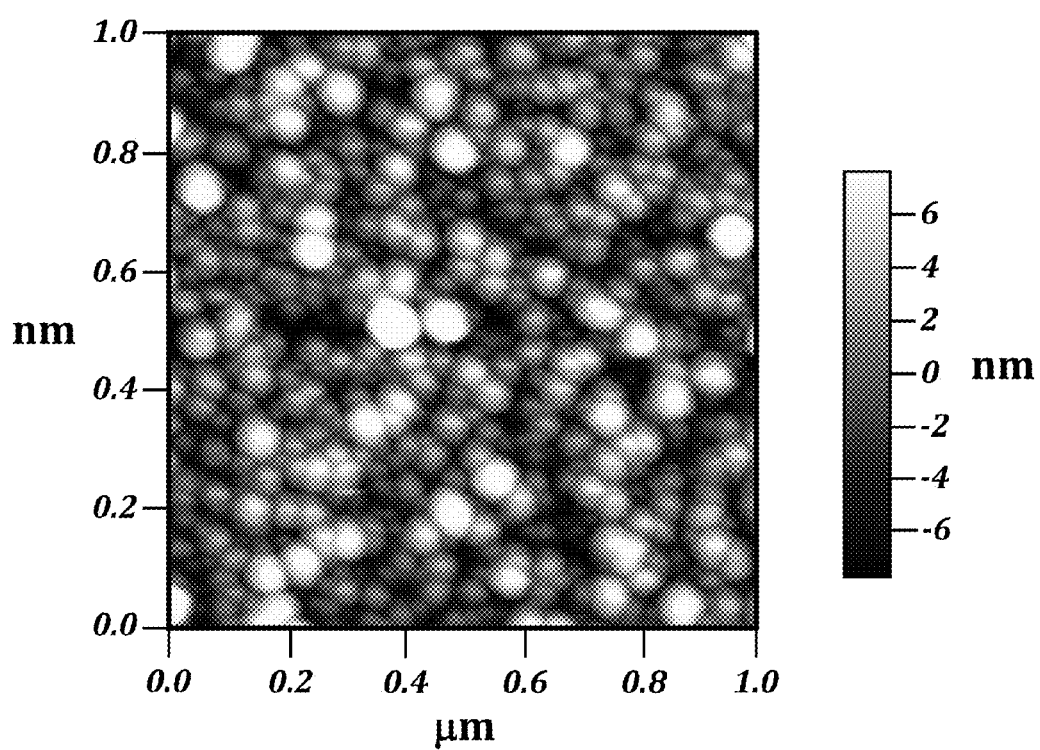
Figure 10C:
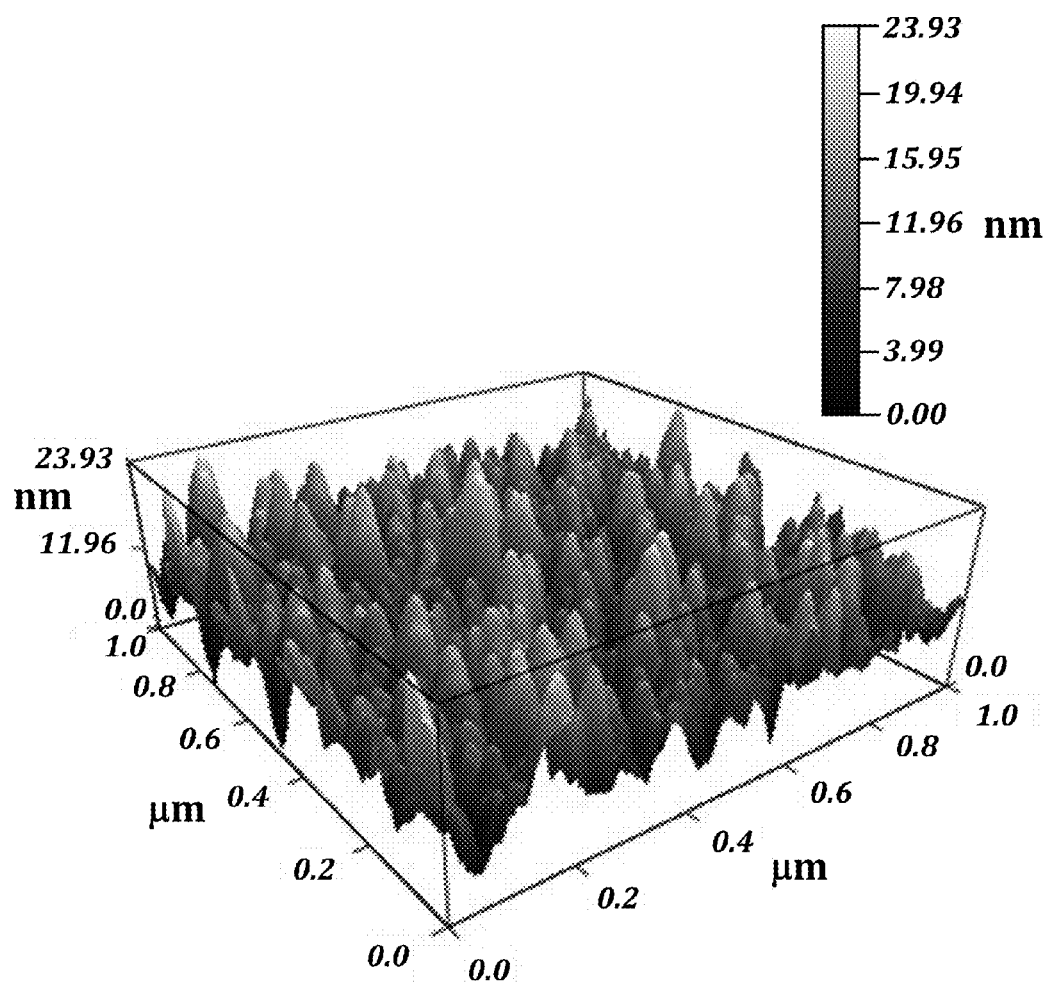
Figure 16:
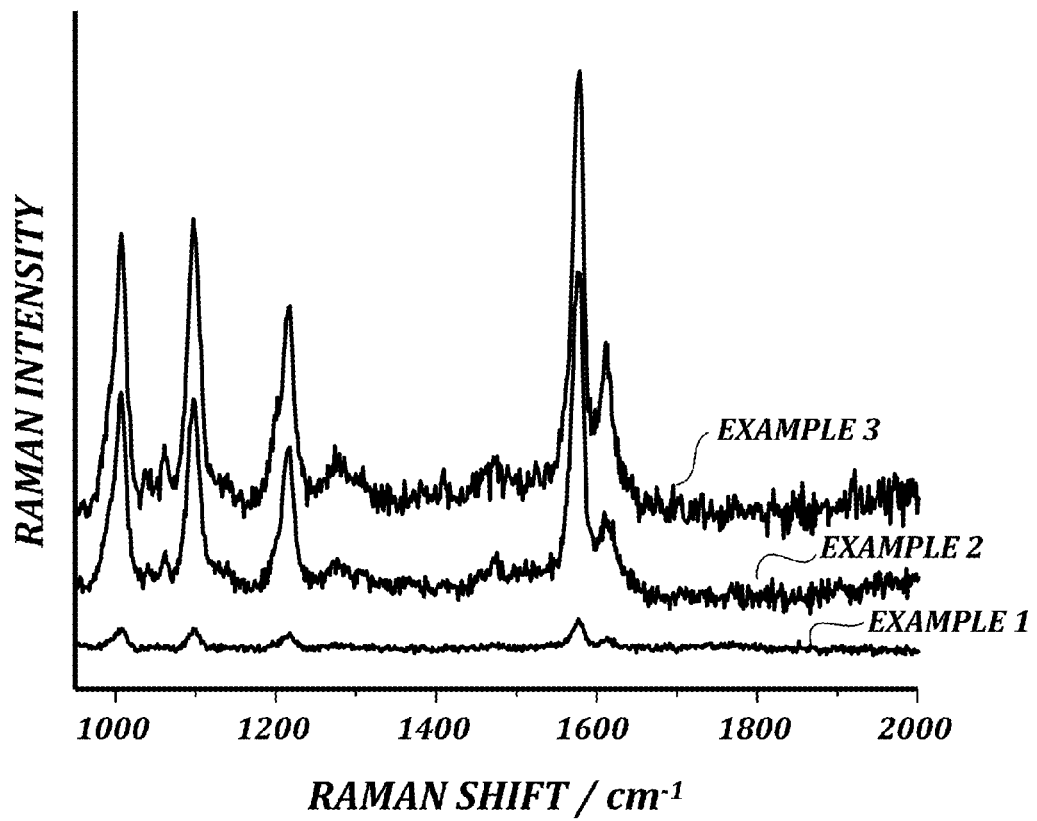
FIG. 16 is a view showing surface enhanced Raman (SERS) spectrum of the samples of Examples 1 to 3.

The obtained sample was observed by AFM. The result is shown in FIGS. 10A-10C. The SERS activity of the sample was examined. The sample was immersed in the solution containing 4-mercaptopyridine (4-MP) as probe molecule and 4-MP was adsorbed to the silver dots. Using the analysis system of FIG. 8, Raman spectrum was measured by the irradiation of laser having wavelength of 514 nm. The result is shown in FIG. 16.

Example 2

Example 2 concerns another SERS substrate in which a ferroelectric single crystal comprises CLN, metallic dots comprise silver dots, and polarization-inverted patterns are periodic.

The experiment was conducted in similar manner to Example 1 except that the irradiation time of the light from mercury xenon lamp was 5 minutes. Similar to Example 1, the SERS activity of the obtained sample was examined. The result is shown in FIG. 16.

Example 3

Example 3 concerns still another SERS substrate in which a ferroelectric single crystal comprises CLN, metallic dots comprise are silver dots, and polarization-inverted patterns are periodic.

Figure 11A:
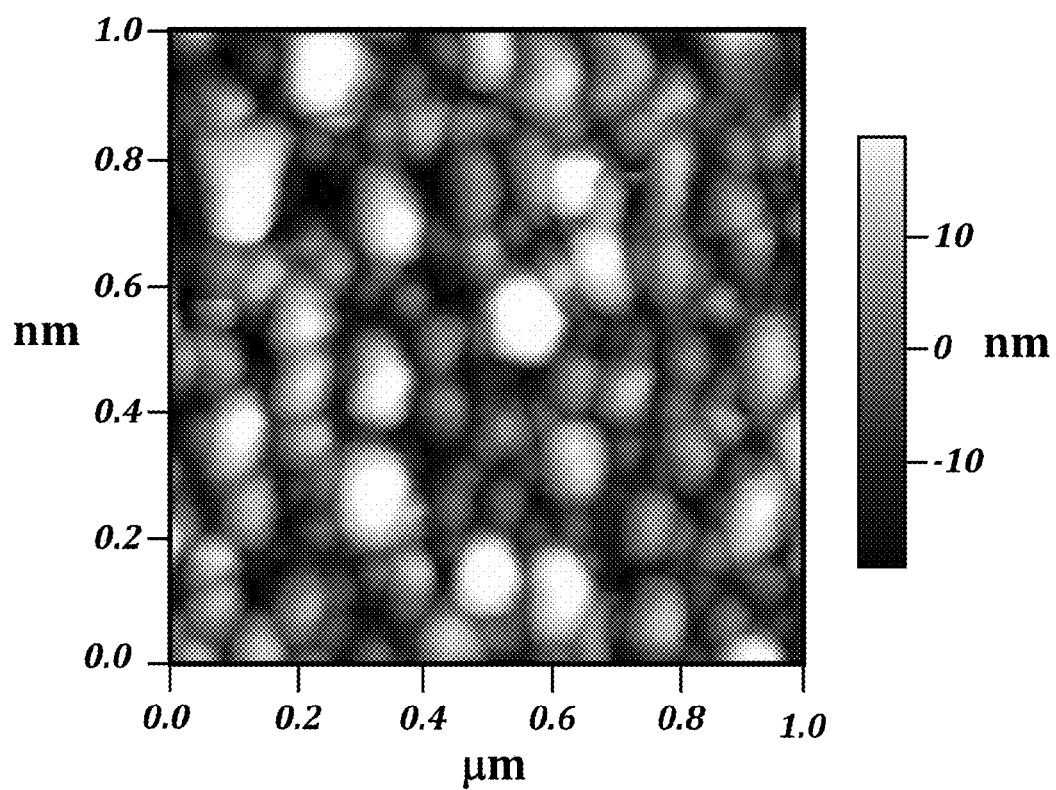
FIGS. 11A and 11B are AFM images of the sample of Example 3.
Figure 11B:
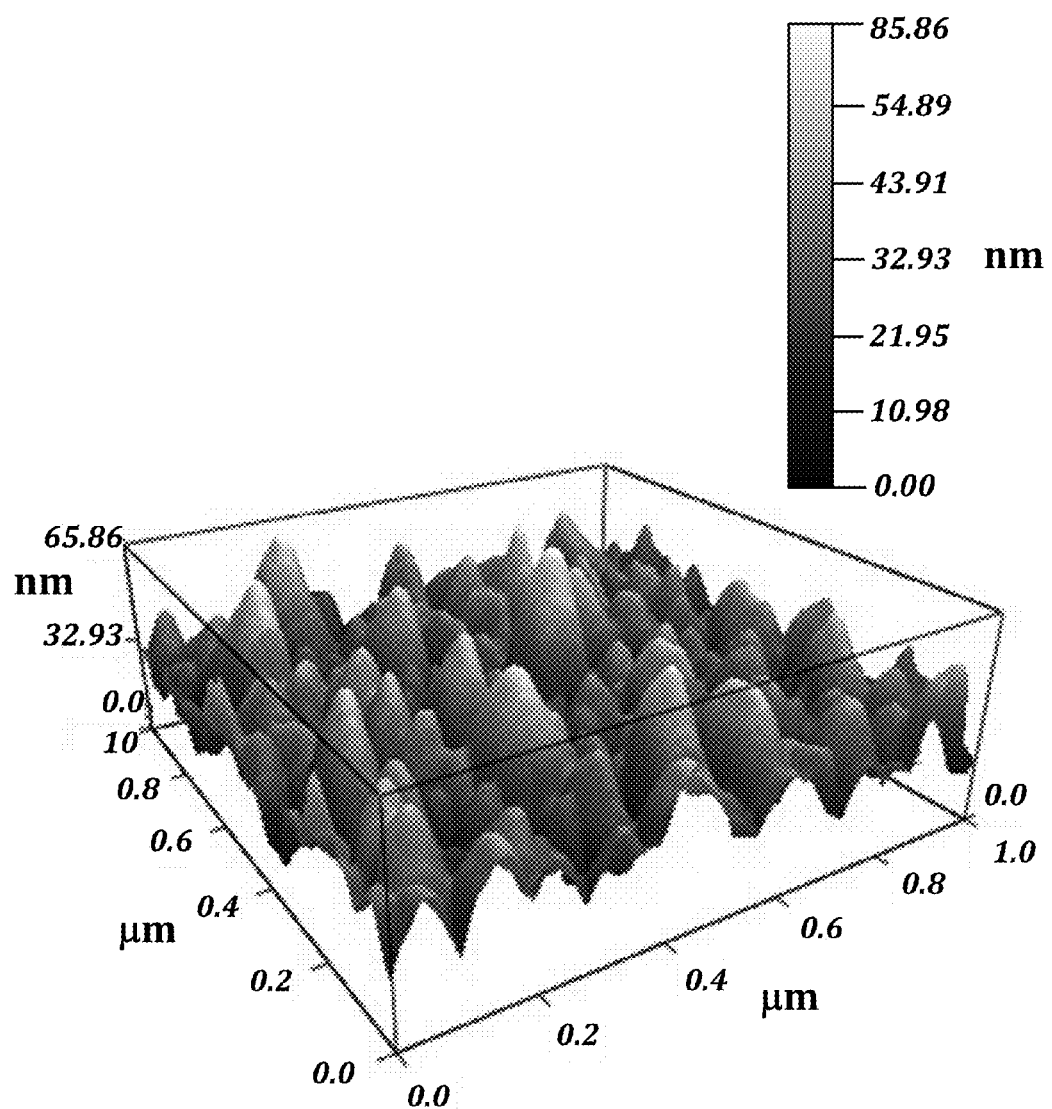
Figure 17:
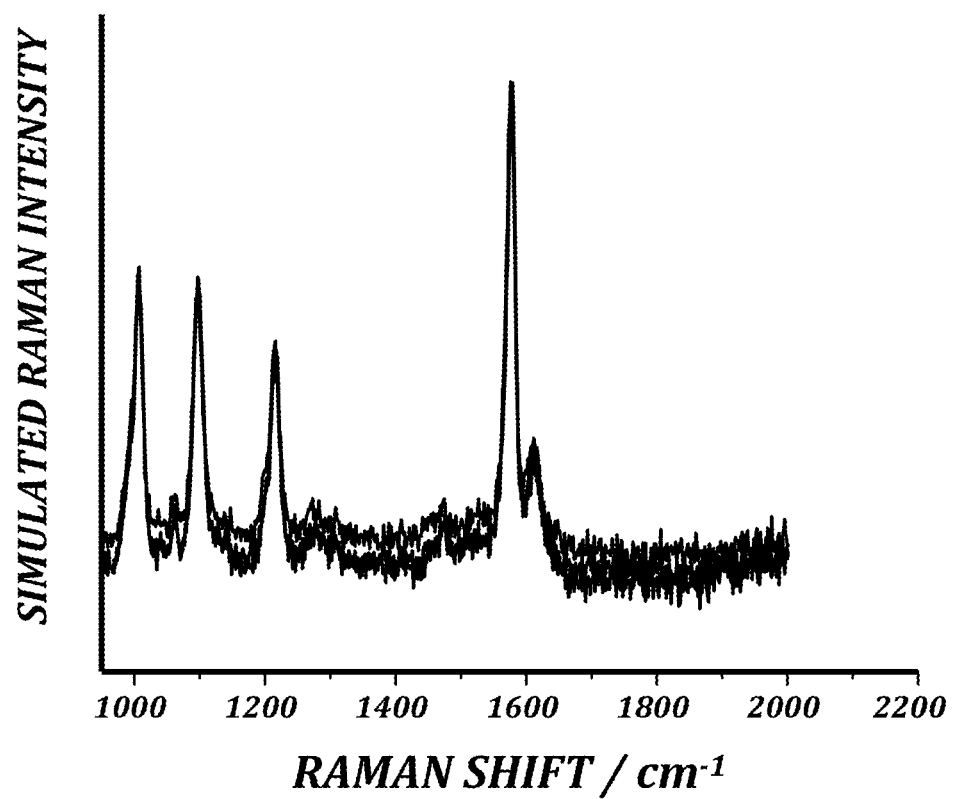
FIG. 17 is a view showing the dependency of measurement positions of Raman spectrum of the sample of Example 3.

The experiment was conducted in similar manner as the Example 1 except that the irradiation time of the light from mercury xenon lamp was 20 minutes. Similar to Example 1, AFM observation and the examination of the SERS activity of the obtained sample were done. The results are shown in FIGS. 11A, 11B, and 16. Further, the uniformity of the obtained sample was examined. The result is shown in FIG. 17.

Example 4

Example 4 concerns still another SERS substrate in which a ferroelectric single crystal comprises CLN, metallic dots comprise gold dots, and polarization-inverted patterns are periodic.

Figure 12A:
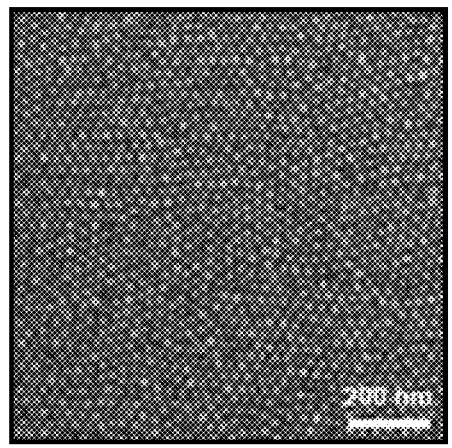
FIG. 12A is a scanning electron microscope (SEM) image and FIGS. 12B-12C are AFM images of the sample of Example 4.

The experiment was conducted in similar manner to the Example 1 except that $HAuCl_4$ aqueous solution ($10^{-4}$ M) was used instead of $AgNO_3$ aqueous solution. The obtained sample was observed by Scanning Electron Microscope (SEM) and AFM. The results are shown in FIGS. 12A (SEM), 12B (AFM), and 12C (AFM). The SERS activity of the obtained sample was examined. The sample was immersed in the solution containing porphyrin as probe molecule, and the porphyrin was adsorbed to the gold dots. Using the analysis system of FIG. 8, Raman spectrum was measured and Scanning Near Field Optical Microscopy (SNOM) was performed. The measurement of Raman spectrum was measured by using laser having wavelengths of 488 nm, 457.9 nm, 514.5 nm, 547.1 nm and 568.2 nm. The results are shown in FIGS. 18A-18C and 19.

Example 5

Example 5 concerns a SERS substrate in which a ferroelectric single crystal comprises CLN, metallic dots comprise silver dots, and polarization-inverted patterns are lattice-shaped.

Reference is made to FIG. 9B. The thickness of the ferroelectric single crystal in the polarization direction was 1 μm. Lattice-shaped polarization-inverted patterns were formed in the CLN substrate by using a piezoresponse scanning method utilizing piezoelectric response. The formation of the lattice-shaped polarization-inverted patterns was confirmed by AFM. The area ratio of the positive polarity surfaces to the negative polarity surfaces (the area of the positive polarity surfaces/the area of the negative polarity surfaces) was about 0.5.

Next, 100 μL of $AgNO_3$ aqueous solution ($10^{-3}$ M) was dropped on the CLN substrate having lattice-shaped polarization-inverted patterns (step S310 of FIG. 3), and the CLN substrate was irradiated with UV light (wavelength of 313 nm, 6 mW) from the mercury xenon lamp (200 W) through a filter for 30 seconds (step S320 of FIG. 3). Excess $AgNO_3$ aqueous solution was removed and dried.

Figure 13A:
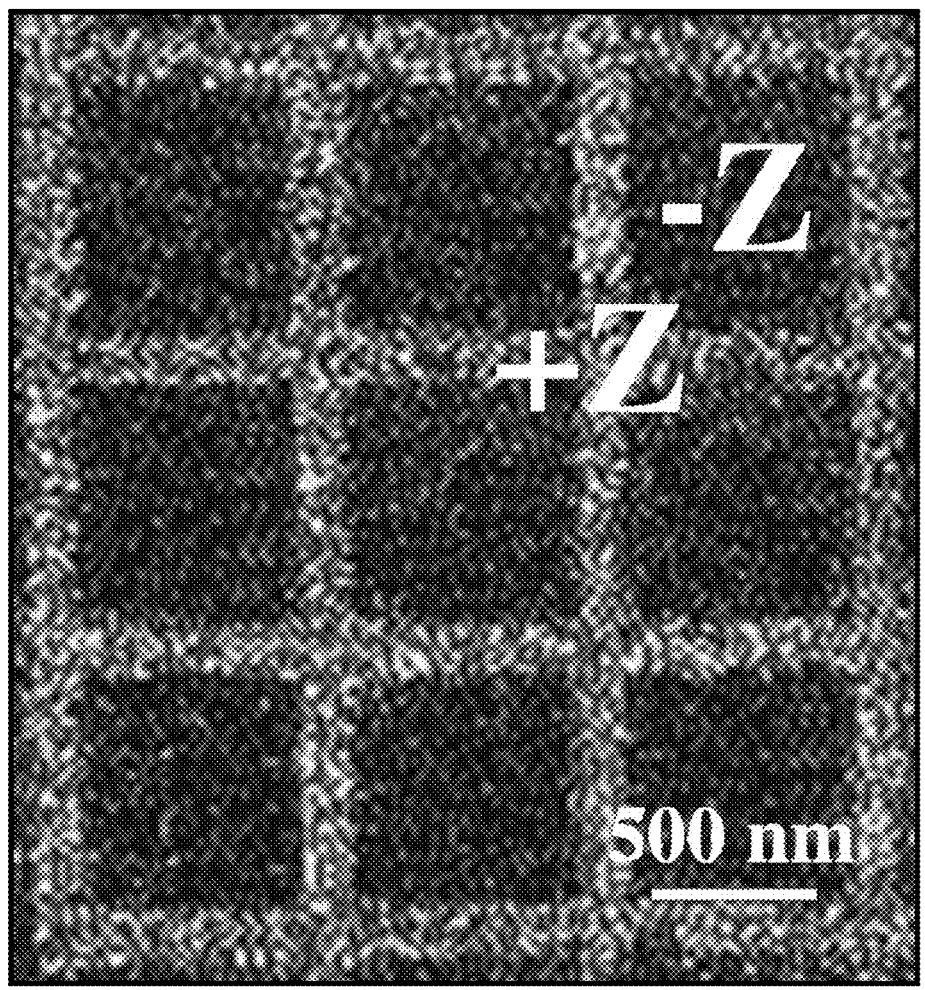
FIGS. 13A-13C are AFM images of the sample of Example 5.
Figure 13B:
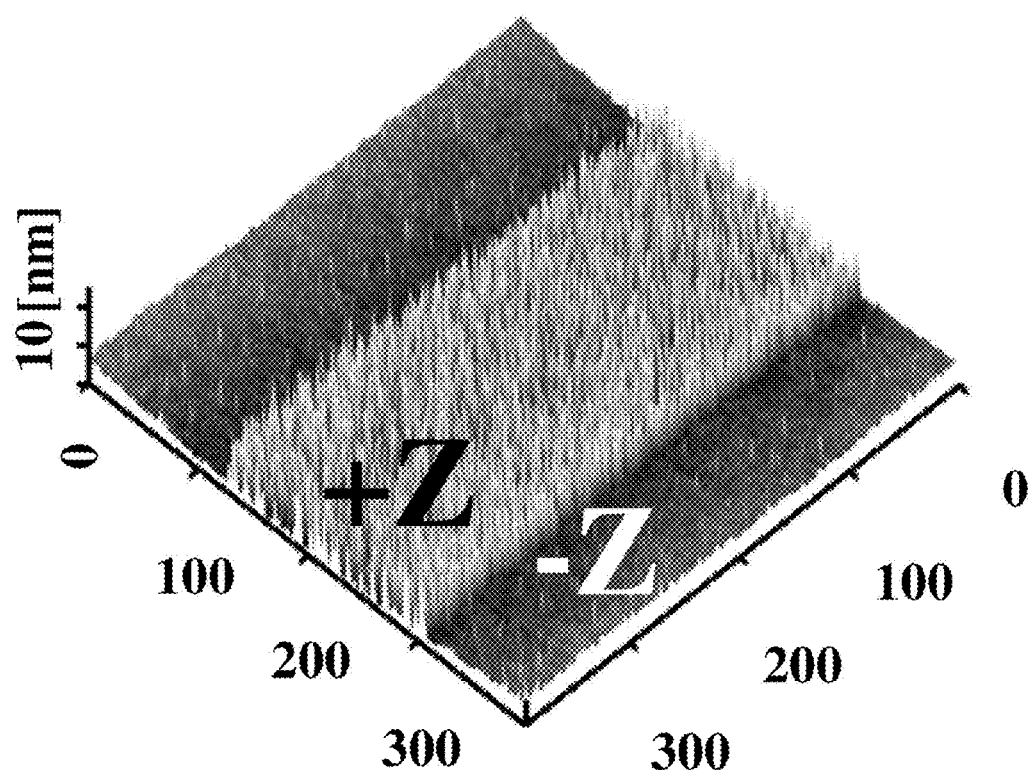
Figure 13C:
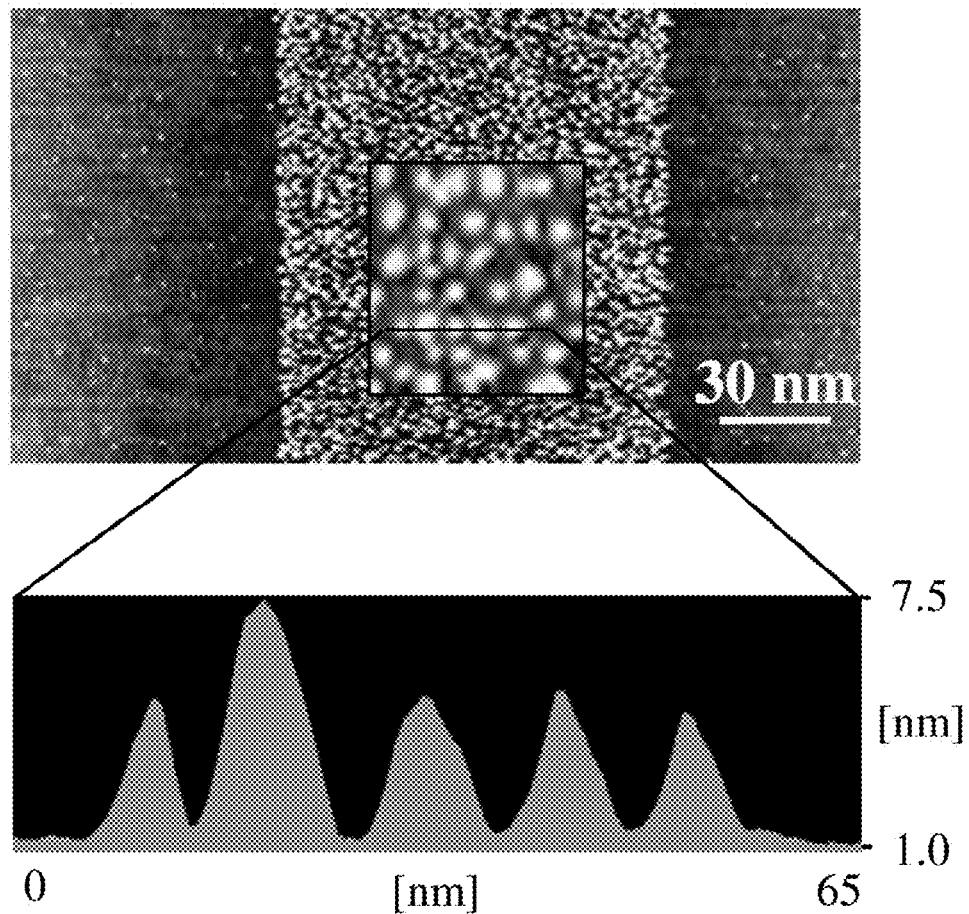

The obtained sample was observed by AFM. The result is shown in FIGS. 13A-13C. Similar to the Example 1, the SERS activity of the obtained sample was examined.

Example 6

Example 6 concerns a SERS substrate in which a ferroelectric single crystal comprises CLN, metallic dots comprise silver dots, and polarization-inverted patterns are dot-shaped.

Figure 14A:
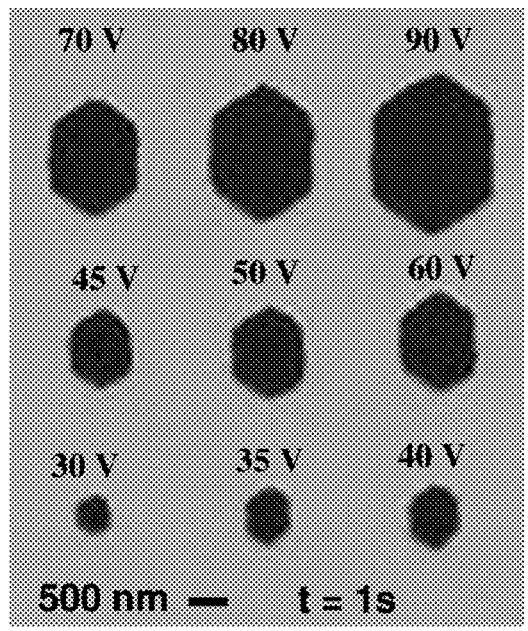
FIG. 14A is an AFM image of a sample of Example 6.

In a similar manner to Example 5, the CLN substrate having dot-shaped polarization-inverted patterns was formed. The surface of the sample was observed by AFM. The result is shown in FIG. 14A. Then, in the similar manner to Example 5, the silver dots were formed on the CLN substrate having the dot-shaped polarization-inverted patterns, and its SERS activity was examined.

Example 7

Example 7 concerns a SERS substrate in which a ferroelectric single crystal comprises SLN, metallic dots comprise silver dots, and polarization-inverted patterns are bar-shaped.

Figure 14B:
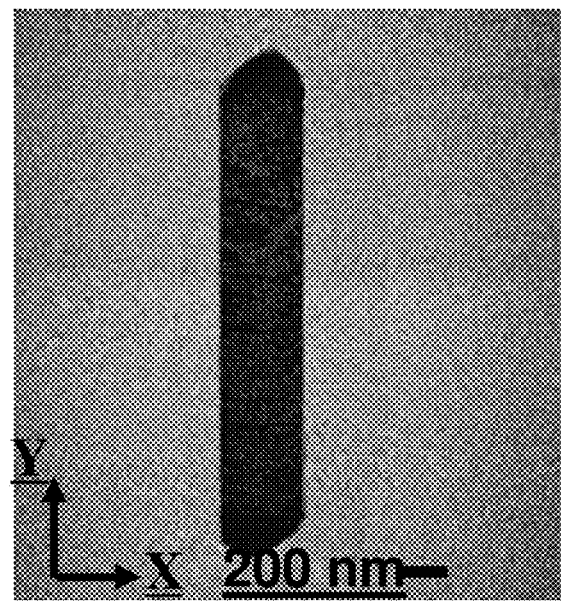
FIG. 14B is an AFM image of a sample of Example 7.

In the similar manner to Example 5, the SLN substrate having the bar-shaped polarization-inverted pattern was formed. The surface of the sample was observed by AFM. The result is shown in FIG. 14B. Then, in the similar manner to Example 5, the silver dots were formed on the SLN substrate having the bar-shaped polarization-inverted patterns, and its SERS activity was examined.

Example 8

Example 8 concerns a SERS substrate in which a ferroelectric single crystal comprises PZT, metallic dots comprise nickel dots, and polarization-inverted patterns are character-shaped.

Figure 15A:
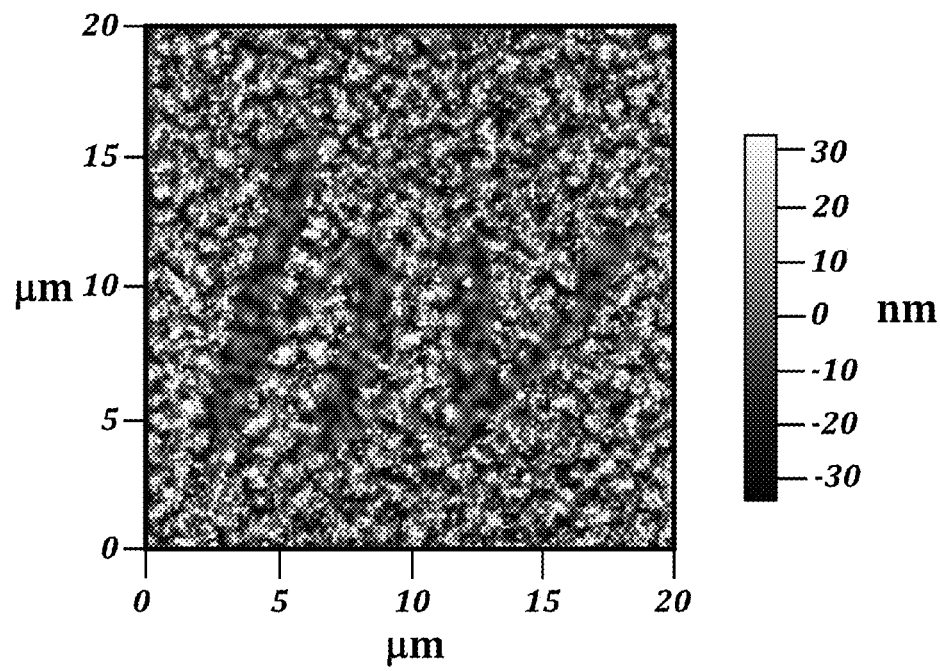
FIGS. 15A and 15B are AFM images of the sample of Example 8.
Figure 15B:
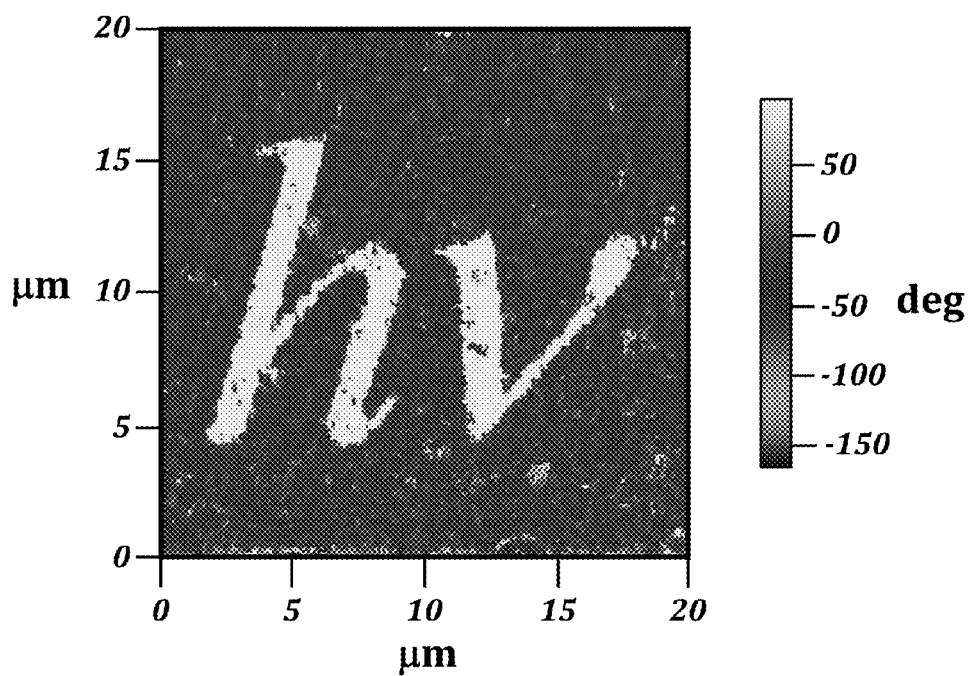

In the similar manner to Example 5 except that the thickness of the ferroelectric single crystal was 500 nm and $NiCl_2 \cdot H_2O$ aqueous solution ($10^{-3}$ M) was used, a PZT substrate having the "hy" character-shaped polarization-inverted patterns was used. Then, in the similar manner to Example 1 except that the light irradiation time was 24 minutes, nickel dots were formed on the PZT substrate having character-shaped polarization-inverted patterns, and the sample was observed by AFM. The result is shown in FIGS. 15A and 15B. Further, its SERS activity was examined.

The above Examples are summarized in Table 1 for simplicity, and the results will be explained below.

TABLE 1

| Example | Ferroelectric crystal | Thickness of crystal | Polarization-inverted patterns | Solution | Concentration of solution (M) | Kind of light | Light intensity | Irradiation time |
|---|---|---|---|---|---|---|---|---|
| Example 1 | CLN | 0.3 mm | periodic | $AgNO_3$ aq. sol. | $10^{-3}$ | white light | 30 W | 3 min. |
| Example 2 | CLN | 0.3 mm | periodic | $AgNO_3$ aq. sol. | $10^{-3}$ | white light | 30 W | 5 min. |
| Example 3 | CLN | 0.3 mm | periodic | $AgNO_3$ aq. sol. | $10^{-3}$ | white light | 30 W | 20 min. |
| Example 4 | CLN | 0.3 mm | periodic | $HAuCl_4$ aq. sol. | $10^{-4}$ | white light | 30 W | 3 min. |
| Example 5 | CLN | 1 μm | lattice-shaped | $AgNO_3$ aq. sol. | $10^{-3}$ | UV light (313 nm) | 6 mW | 30 sec. |
| Example 6 | CLN | 1 μm | dot-shaped | $AgNO_3$ aq. sol. | $10^{-3}$ | UV light (313 nm) | 6 mW | 30 sec. |
| Example 7 | SLN | 1 μm | bar-shaped | $AgNO_3$ aq. sol. | $10^{-3}$ | UV light (313 nm) | 6 mW | 30 sec. |
| Example 8 | PZT | 500 nm | character-shaped | $NiCl_2$ aq. sol. | $10^{-3}$ | white light | 30 W | 24 min. |

FIGS. 10A-10C are AFM images of the sample of Example 1.

In FIG. 10A, the regions indicated with bright contrast are the positive polarity surfaces (+Z) of the polarization-inverted portions and the regions indicated with dark contrast are the negative polarity surfaces (-Z) of the non-inverted polarization portions. It was confirmed from FIG. 10A that the periodic polarization-inverted portions were maintained after depositing the silver dots. FIG. 10B is an enlarged view of a part of +Z surfaces of FIG. 10A. It is seen from FIG. 10B that the silver dots are positioned on the positive polarity surfaces. As seen from FIGS. 10B and 10C that the shape of each of the silver dots was conical and the dot diameter $N_D$ and the dot interval $N_B$ were 30 nm, respectively. Also, it was confirmed that the silver dots did not exist on the negative polarity surfaces.

FIGS. 11A and 11B are AFM images of the sample of Example 3.

FIGS. 11A and 11B indicate that the conical-shape silver dots are positioned on the positive polarity surfaces (+Z) and the dot diameter $N_D$ and the dot interval $N_B$ are 100 nm, respectively. Also, it was confirmed that the silver dots did not exist on the negative polarity surfaces. Although not shown, it was confirmed that the silver dots of the Example 2 having the dot diameter $N_D$ and the dot interval $N_B$ of 70 nm, respectively existed on the positive polarity surfaces.

Figure 12B:
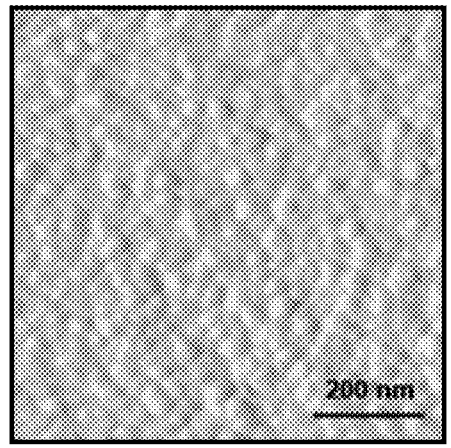
Figure 12C:
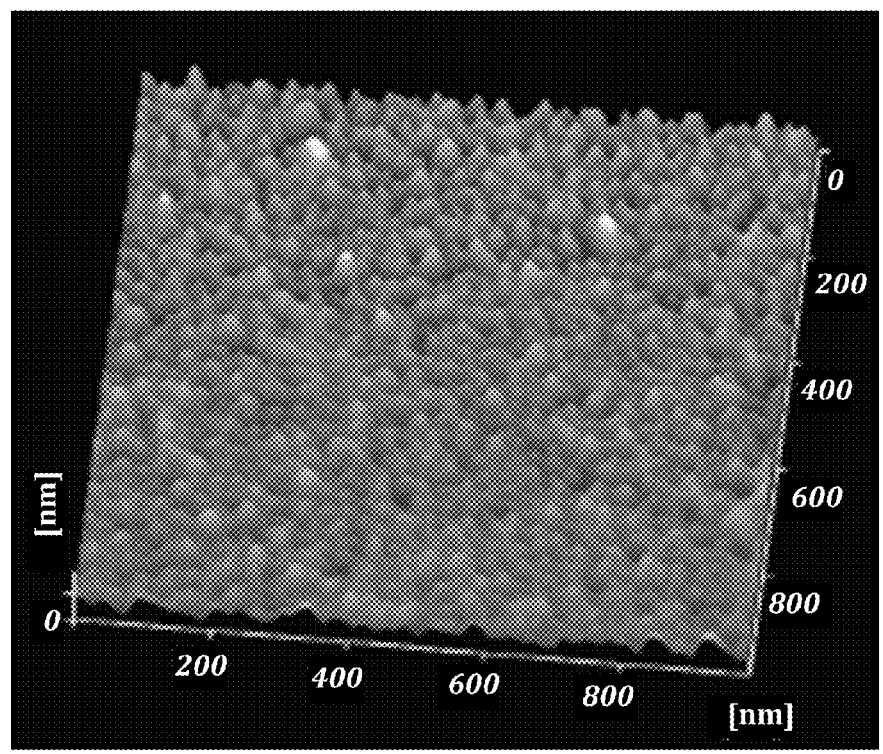

FIG. 12A is an SEM image and FIGS. 12B and 12C are AFM images, of the sample of Example 4.

It is understood from the SEM image of FIG. 12A that the gold dots are positioned on the CLN substrate uniformly. The AFM images of FIGS. 12B and 12C indicate that the conical-shaped gold dots are positioned on the positive polarity surfaces (+Z) of the CLN substrate, and the dot diameter $N_D$ and the dot interval $N_B$ of 30 nm, respectively. Although not shown, it was confirmed that the gold dots did not exist on the negative polarity surfaces (-Z).

FIGS. 13A-13C are AFM images of the sample of Example 5.

In FIG. 13A, the regions indicated with bright contrast are the positive polarity surfaces (+Z) of the polarization-inverted portions and the regions indicated with dark contrast are the negative polarity surfaces (−Z) of the non-inverted polarization portions. It was confirmed from FIG. 13A that the lattice-shaped polarization-inverted portions were maintained after depositing the silver dots. It is seen from FIG. 13B that the silver dots were positioned only on +Z surfaces and the silver dots were not positioned on −Z surfaces. As seen from FIGS. 13B and 13C that the shape of each of the silver dots was conical and the dot diameter $N_D$ and the dot interval $N_B$ were 10 nm, respectively.

FIG. 14A shows AFM image of the sample of Example 6 before depositing the silver dots, and FIG. 14B shows AFM image of the sample of Example 7 before depositing the silver dots. It was confirmed from FIG. 14A that the dot-shaped polarization-inverted patterns were formed, and the surface ratio of the positive polarity surfaces to the negative polarity surfaces (the area of the positive polarity surfaces/the area of the negative polarity surfaces) is 0.3. It was confirmed from FIG. 14B that the bar-shaped polarization-inverted patterns were formed and the surface ratio of the positive polarity surfaces to the negative polarity surfaces was 0.25.

It was confirmed that the silver dots were positioned on +Z surfaces of the CLN substrate having the dot-shaped polarization-inverted patterns and the SLN substrate having the bar-shaped polarization-inverted patterns.

FIGS. 15A and 15B are AFM images of the sample of Example 8.

In FIGS. 15A and 15B, the regions indicated by "hγ" are the positive polarity surfaces (+Z) of the polarization-inverted portions, and the regions other than the regions indicated by "hγ" are the negative polarity surfaces (−Z) of the non-inverted polarization portions. It was confirmed that the area ratio of the positive polarity surfaces to the negative polarity surfaces was 0.3. It was confirmed that from FIGS. 15A and 15B that the character-shaped polarization-inverted patterns were maintained after depositing the nickel dots. Further, it is understood that the nickel dots were positioned only on the −Z surfaces, and the nickel dots were not positioned on the +Z surfaces.

As mentioned above, by adopting the manufacturing method of the invention (FIGS. 3 and 4), it was indicated that the substrate comprised of the ferroelectric single crystal having the polarization-inverted patterns of the spontaneous polarizations, including the polarization-inverted portions and the non-inverted polarization was obtained in which the metallic dots were positioned on either one polarized surfaces of the polarization-inverted portions and the non-inverted polarization.

Further, it was found that the polarization-inverted patterns were not limited specifically. It was also found that when the area ratio of the positive polarity surfaces to the negative surfaces (the area of the positive polarity surfaces/the area of the negative polarity surfaces) was in the range of from 0.25 to 4, the metallic dots were positioned with certainty.

Further, it was confirmed that according to the manufacturing method of the invention, the metallic dots had the dot diameter $N_D$ and the dot interval $N_B$ within the range of from 10 nm to 200 nm, and were distributed uniformly. Although silver (Ag), gold (Au) and nickel (Ni) as a typical metal used for the metallic dots are explained above, Pt, Pd, Rh, Co, Fe or an alloy thereof may deposited on the ferroelectric single crystal by adopting the manufacturing method of the invention. Further, the dot diameter and the dot interval of the metallic dots to be deposited can be controlled by adjusting the concentration of the solution, the light intensity and the light irradiation time in the manufacturing method of the invention.

FIG. 16 is a view showing surface enhanced Raman (SERS) spectrum of the samples of Examples 1 to 3.

It was found that each of the Raman spectra coincided with that of 4-PM, respectively, and each sample had the SERS activity. Specifically, it was found that the peak intensities were increased, namely, the SERS activities were enhanced, in the order of increasing enhancement: Example 1, Example 2 and Example 3. Since the enhancement effect of the SERS activity is most extremely high in Example 3 having the average dot diameter of 100 nm, the extremely high enhancement effect can be obtained when the average dot diameter is in the range of from 50 nm to 150 nm. It was confirmed that the samples of Examples 5 to 8 had the SERS activities, similarly.

FIG. 17 is a view showing the dependency of measurement position of Raman spectrum of the sample of Example 3, with Raman spectra from three different positions on the sample. The Raman spectra are nearly identical, as illustrated in FIG. 17. From this, it was found that by adopting the manufacturing method of the invention (FIGS. 3 and 4), the SERS substrate enabled to conduct the measurement uniformly and stably could be obtained.

Figure 18A:
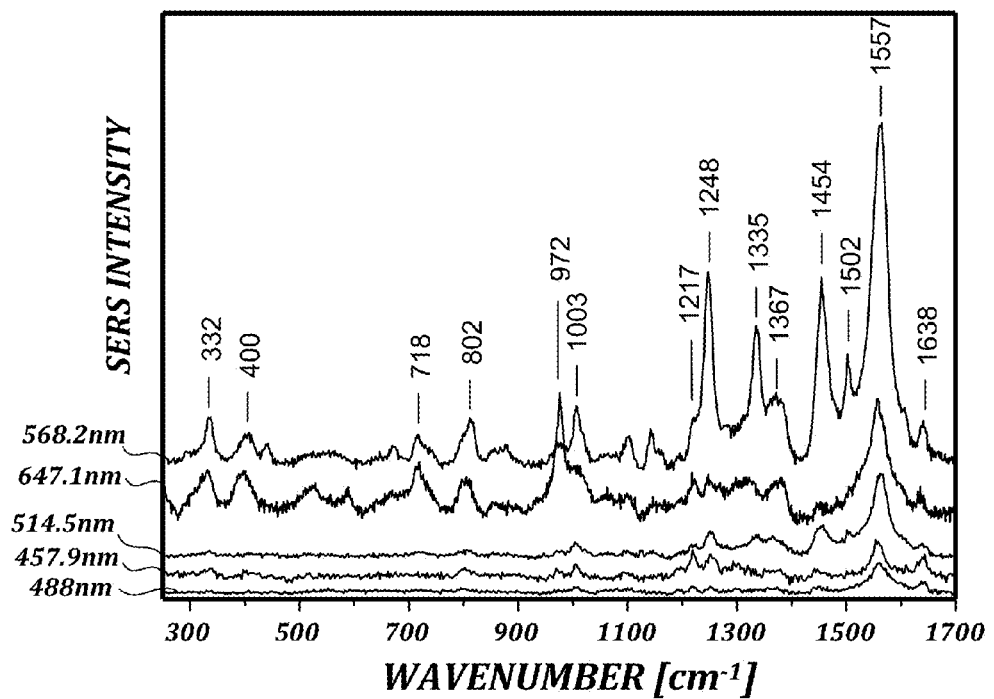
FIG. 18A is surface enhanced Raman (SERS) spectra of the sample of Example 4.
Figure 18B:
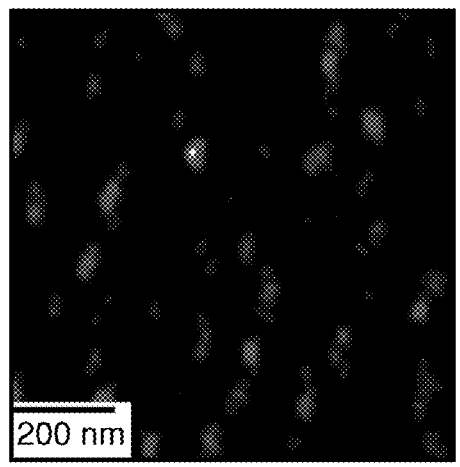
FIGS. 18B and 18C are SNOM image of the sample of Example 4.
Figure 18C:
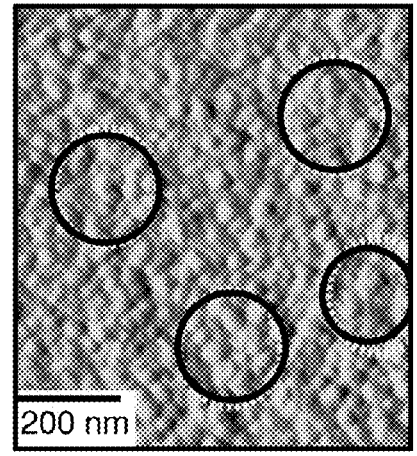

FIG. 18A are surface enhanced Raman (SERS) spectra, and FIGS. 18B and 18C are SNOM images, of the sample of Example 4.

FIG. 18A indicates that the obtained Raman spectrum coincided with Raman spectrum of porphyrin. Especially, high Raman activity was expressed in the wavelength of beyond 515 nm. The regions indicated with bright contrast in FIG. 18B and the regions surrounded by circles in FIG. 8C were "hot spots" indicating that the SERS were enhanced. Since there were many hot spots, it is understood that the SERS substrate of the invention had an extremely high enhancement effect.

Figure 19:
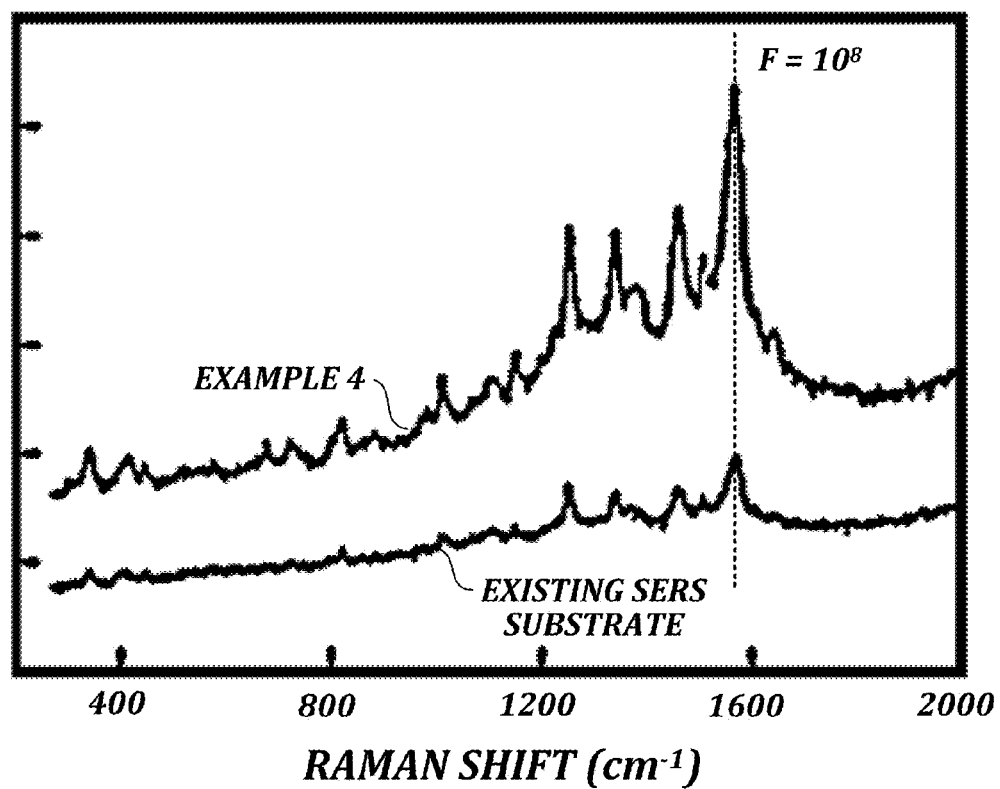
FIG. 19 is a view showing surface enhanced Raman (SERS) spectrum of the samples of Example 4 and the existing SERS substrate.

FIG. 19 is a view showing the surface enhanced Raman (SERS) spectrum of the samples of Example 4 and the existing SERS substrate. As the existing SERS substrate, SERS substrate (manufactured by IMRA AMERICA) was used. The wavelength used was 568.2 nm. As shown in FIG. 19, the SERS substrate of the invention exhibited an extremely high enhancement effect ($10^8$) when compared with the existing SERS substrate.

The substrate comprising the ferroelectric material having the polarization-inverted patterns of the spontaneous polarizations, including the polarization-inverted portions and the non-inverted polarization portions, in which the metallic dots were positioned on only either one polarized surfaces of the polarization-inverted portions and the non-inverted polarization portions had SERS activity, and were effective as SERS substrate. It was found that the SERS substrate of the invention that an increase in dot diameter $N_D$ and/or dot interval $N_B$ results in higher SERS activity. The dot diameter $N_D$ was preferably in the range of from 50 nm to 150 nm. The dot interval $N_B$ was preferably in the range of from 50 nm to 150 nm.

Example 9

Example 9 concerns a microfluidic device provided with the SERS substrate manufactured in Example 4.

Figure 20A:
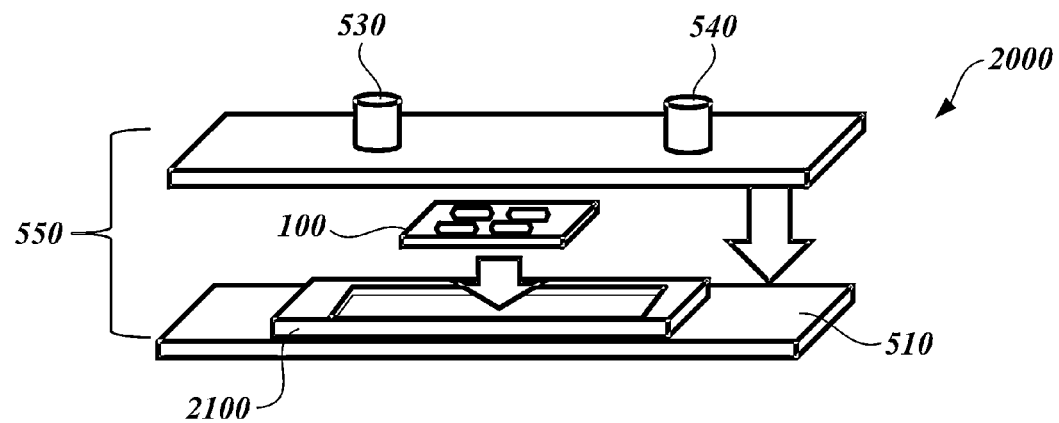
FIGS. 20A and 20B are schematic views of the microfluidic device manufactured in Example 9.
Figure 20B:
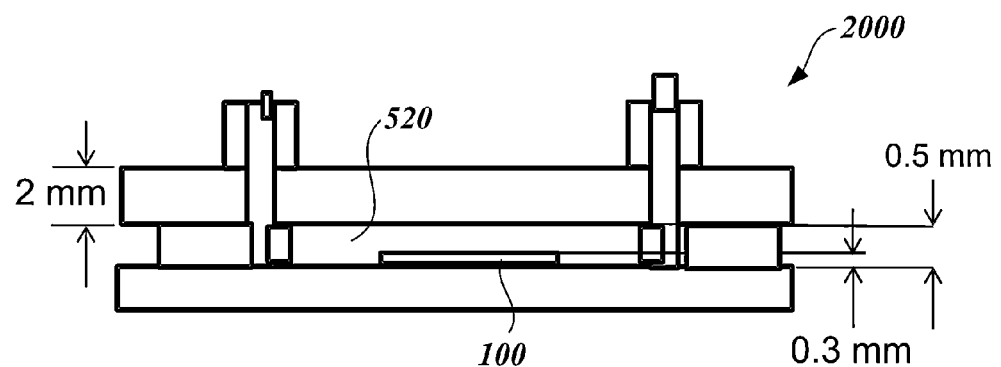

FIGS. 20A and 20B are schematic views of the microfluidic device manufactured in Example 9.

Figure 21:
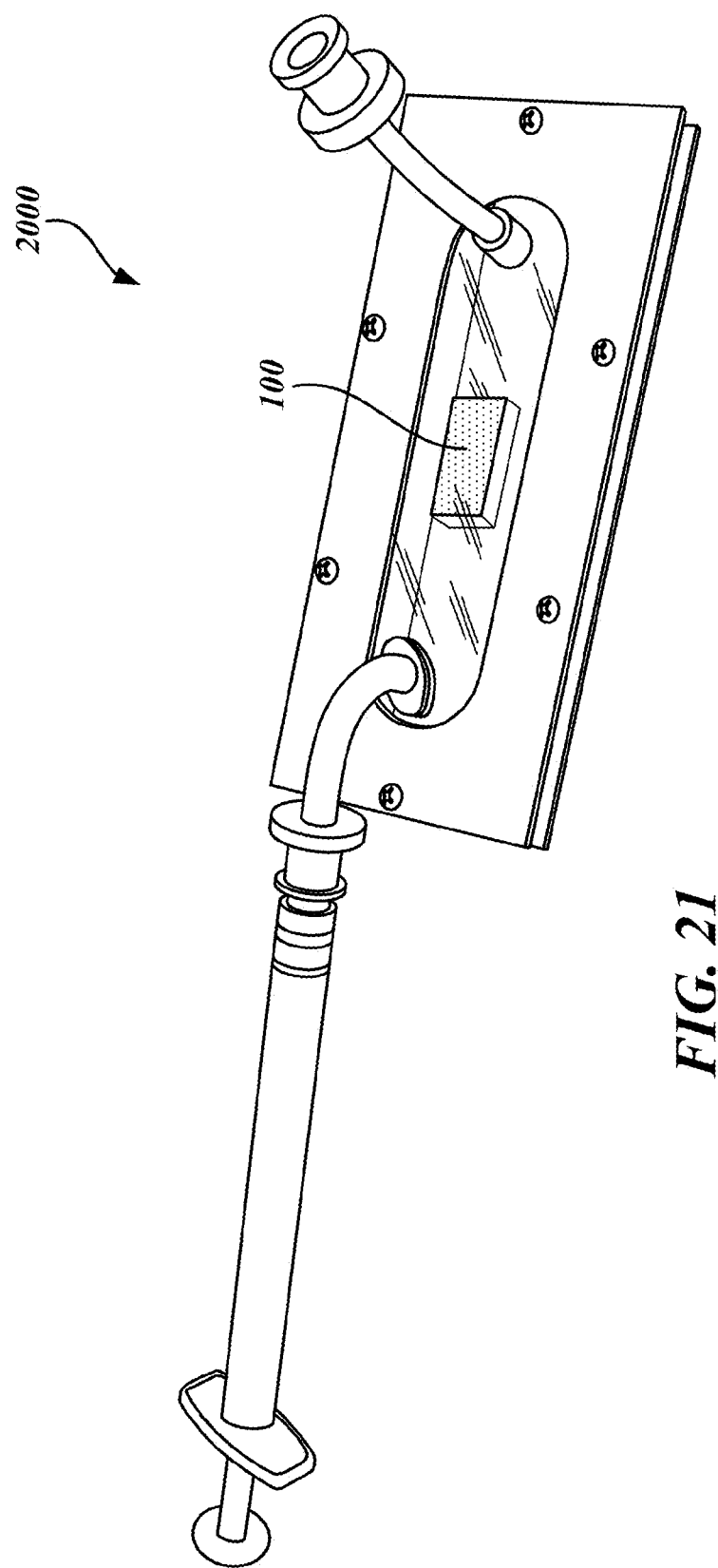
FIG. 21 is a view showing an external appearance of the microfluidic device manufactured in Example 9.

FIG. 21 is a view showing an external appearance of the microfluidic device manufactured in Example 9.

As shown in FIGS. 20A and 20B, a microfluidic device 2000 of the invention was designed. The microfluidic device 2000 is provided with a slide glass as the base plate 510 and the microfluidic path 520 formed on the base plate 510 in which fluid flows, and the SERS substrate manufactured in Example 4 as the SERS substrate 100 is disposed on the base plate 510. The base plate 510, the microfluidic path 520, and SERS substrate 100 are disposed in the housing 550 made of silica glass and provided with the inlet port 530 and the drain port 540. Further, the microfluidic path 520 is sealed with a silicone ring 2100.

FIG. 21 shows an external appearance of the microfluidic device 2000 having the inlet port 530 to which a microsyringe containing peptide therein is attached and the drain port 540 to which a liquid reservoir is attached.

Using the microsyringe, a peptide was injected into the microfluidic path 520 through the inlet port 530, and the peptide was adsorbed to the SERS substrate 100. By using the analysis system of FIG. 8 and a laser with a wavelength of 568.2 nm, the surface enhanced Raman (SERS) spectrum of the SERS substrate 100 before and after making the peptide to flow through the microfluidic path 520 were measured. The results are shown in FIG. 22.

Figure 22:
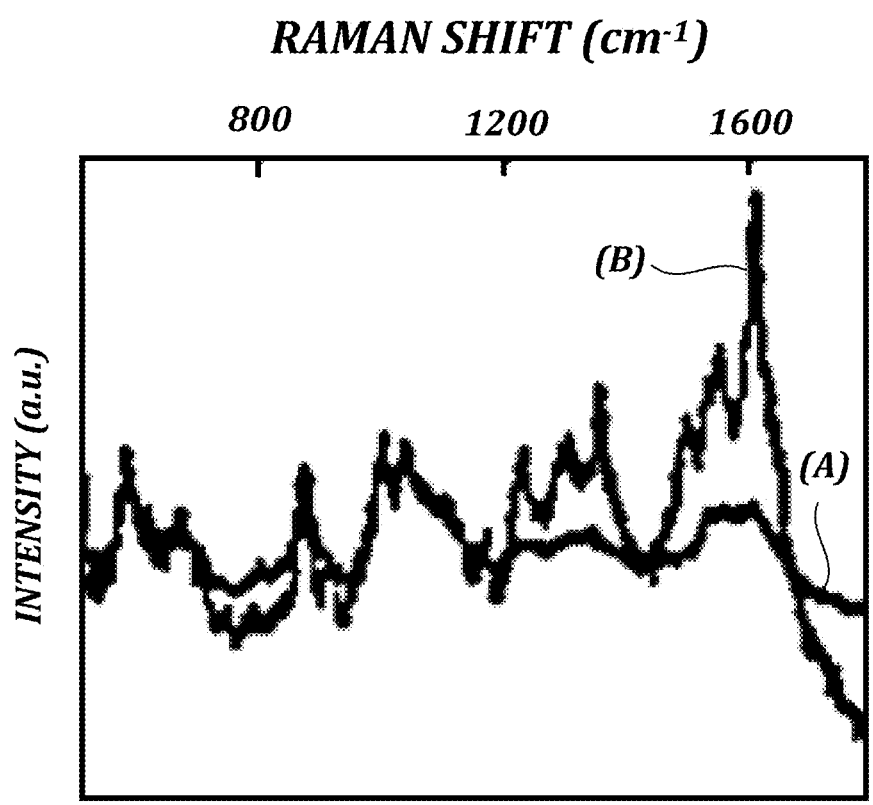
FIG. 22 is a view showing surface enhanced Raman (SERS) spectrum of the SERS substrate using the microfluidic device of the Example 9 of the invention.

FIG. 22 is a view showing the surface enhanced Raman (SERS) spectrum of the SERS substrate using the microfluidic device of the Example 9.

In FIG. 22, the spectrum (A) represents Raman spectrum of the SERS substrate 100 before making the peptide to flow through the microfluidic path 520, and the spectrum (B) represents Raman spectrum of the SERS substrate 100 after making the peptide to flow through the microfluidic path 520.

The Raman spectrum of the SERS substrate 100 changed from the spectrum (A) to the spectrum (B) by making the peptide to flow. Further, the spectrum (B) coincided with Raman spectrum of the peptide. From this, it was found that SERS substrate and the microfluidic device using the same of the invention can serve as a biosensor.

The embodiments of the invention in which an exclusive property or privilege is claimed are defined as follows:

1. A substrate for surface enhanced Raman spectroscopy analysis, comprising a ferroelectric single crystal having polarization-inverted patterns of spontaneous polarizations including polarization-inverted portions and non-inverted polarization portions; and metallic dots positioned on only one of the polarized surfaces selected from the group consisting of the polarization-inverted portions and the non-inverted polarization portions,
    wherein the metallic dots have diameter of from 50 nm to 150 nm and the metallic dots are positioned at an interval of from 50 nm to 150 nm.

2. The substrate for surface enhanced Raman spectroscopy analysis according to claim 1, wherein the ferroelectric single crystal is a lithium niobate, a lithium tantalate or a lead zirconate.

3. The substrate for surface enhanced Raman spectroscopy analysis according to claim 1, wherein the polarization-inverted patterns satisfy a condition that an area ratio of the positive polarity surfaces to the negative polarity surfaces is in a range of from 0.25 to 4.

4. The substrate for surface enhanced Raman spectroscopy analysis according to claim 1, wherein the metallic dots comprise one member selected from the group consisting of Au, Ag, Pt, Pd, Rh, Ni, Co, Fe and an alloy thereof.

5. A manufacturing method of a substrate for surface enhanced Raman spectroscopy analysis according to claim 1, comprising:
    a step of providing a solution including metal to a ferroelectric single crystal having polarization-inverted patterns of spontaneous polarizations including polarization-inverted portions and non-inverted polarization portions; and
    a step of irradiating the ferroelectric single crystal provided with the solution with a light.

6. The manufacturing method of a substrate for surface enhanced Raman spectroscopy analysis according to claim 5, wherein a concentration of the solution is in the range of from $10^{-4}$ M to $10^{-3}$ M.

7. The manufacturing method of a substrate for surface enhanced Raman spectroscopy analysis according to claim 5, wherein the light is ultraviolet light, a visible light or white light.

8. The manufacturing method of a substrate for surface enhanced Raman spectroscopy analysis according to claim 5, wherein the irradiation time in the step of irradiating the ferroelectric single crystal with the light is from 30 seconds to 25 minutes.

9. A biosensor using the substrate for surface enhanced Raman spectroscopy analysis according to claim 1.

10. A microfluidic device for surface enhanced Raman spectroscopy analysis, including:
    a base plate; and
    a microfluidic path formed on the base plate in which fluid flows; and wherein
    a substrate for surface enhanced Raman spectroscopy analysis according to claim 1 is provided on the base plate.

11. A microfluidic device for surface enhanced Raman spectroscopy analysis, including:
    a base plate; and
    a microfluidic path formed on the substrate in which fluid flows; and wherein
    the base plate comprises a ferroelectric single crystal;
    wherein at least one portion of the ferroelectric single crystal has a substrate for surface enhanced Raman spectroscopy analysis according to claim 1.

* * * * *